United States Patent
Nakamura et al.

(10) Patent No.: US 11,787,421 B2
(45) Date of Patent: Oct. 17, 2023

(54) MOTION SICKNESS ESTIMATION DEVICE, MOTION SICKNESS REDUCING DEVICE AND MOTION SICKNESS ESTIMATION METHOD

(71) Applicant: Mitsubishi Electric Corporation, Tokyo (JP)

(72) Inventors: Yudai Nakamura, Tokyo (JP); Masahiro Naito, Tokyo (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 212 days.

(21) Appl. No.: 17/310,219

(22) PCT Filed: Jan. 9, 2020

(86) PCT No.: PCT/JP2020/000455
§ 371 (c)(1),
(2) Date: Jul. 27, 2021

(87) PCT Pub. No.: WO2020/170640
PCT Pub. Date: Aug. 27, 2020

(65) Prior Publication Data
US 2022/0135054 A1    May 5, 2022

(30) Foreign Application Priority Data

Feb. 18, 2019    (JP) .................................. 2019-026470

(51) Int. Cl.
*B60W 50/00* (2006.01)
*B60W 40/09* (2012.01)
(Continued)

(52) U.S. Cl.
CPC ........ *B60W 50/0098* (2013.01); *B60W 40/09* (2013.01); *G06V 20/597* (2022.01);
(Continued)

(58) Field of Classification Search
CPC ...... A61B 5/1114; A61B 5/18; B60W 30/182; B60W 40/08; B60W 40/09;
(Continued)

(56) References Cited

U.S. PATENT DOCUMENTS 6,042,533 A * 3/2000 Kania ............... A61M 21/0094
600/27
7,918,781 B1 * 4/2011 Smyth .................. A61M 21/00
600/27
(Continued)

FOREIGN PATENT DOCUMENTS

JP    2000-52735 A       2/2000
JP    2000085332 A  *    3/2000
(Continued)

OTHER PUBLICATIONS

International Search Report and Written Opinion dated Mar. 10, 2020, received for PCT Application PCT/JP2020/000455, Filed on Jan. 9, 2020, 11 pages including English Translation.
(Continued)

*Primary Examiner* — Peter D Nolan
*Assistant Examiner* — Ce Li Li
(74) *Attorney, Agent, or Firm* — XSENSUS LLP

(57) ABSTRACT

A motion sickness estimation device including processing circuitry configured to calculate a sensory conflict amount on a basis of a motion of an occupant's head caused by vibration of a vehicle; extract a feature of a traveling situation on a basis of at least one of the motion of the occupant's head or a motion of the vehicle; determine a habituation progress state, which is a state in which the occupant's habituation to the traveling situation has progressed, on a basis of biometric information of the occupant; set sensitivity to the feature of the traveling situation on a basis of the habituation progress state; correct the sensory conflict amount on a basis of the sensitivity; and estimate a motion sickness state of the occupant on a basis of the sensory conflict amount that has been corrected.

18 Claims, 10 Drawing Sheets

(51) Int. Cl.
*G06V 20/59* (2022.01)
*B60W 40/08* (2012.01)

(52) U.S. Cl.
CPC ............... *B60W 2040/0881* (2013.01); *B60W 2540/223* (2020.02); *B60W 2540/227* (2020.02)

(58) Field of Classification Search
CPC ..... B60W 50/0098; B60W 2040/0872; B60W 2040/0881; B60W 2050/0075; B60W 2420/42; B60W 2540/223; B60W 2540/227; G06V 20/597
See application file for complete search history.

(56) References Cited

U.S. PATENT DOCUMENTS

| | | | | |
|---|---|---|---|---|
| 8,708,884 | B1* | 4/2014 | Smyth | G06F 3/011 706/15 |
| 9,809,115 | B2* | 11/2017 | Mäder | G08B 21/06 |
| 10,730,524 | B2* | 8/2020 | Frye | B60R 21/01512 |
| 2011/0282130 | A1* | 11/2011 | Krueger | A61B 5/1114 600/27 |
| 2014/0152792 | A1* | 6/2014 | Krueger | A61B 5/4863 348/78 |
| 2016/0167672 | A1* | 6/2016 | Krueger | G16H 40/63 340/576 |
| 2017/0150930 | A1 | 6/2017 | Shikii et al. | |
| 2017/0291538 | A1* | 10/2017 | Sivak | A61M 21/02 |
| 2018/0178808 | A1* | 6/2018 | Zhao | B60K 28/066 |
| 2019/0202324 | A1* | 7/2019 | Ketels | B60N 2/72 |
| 2020/0324675 | A1* | 10/2020 | Yamamoto | B60N 2/90 |
| 2020/0353934 | A1* | 11/2020 | Vulcu | A61B 5/165 |

FOREIGN PATENT DOCUMENTS

| | | | |
|---|---|---|---|
| JP | 2012-131269 | A | 7/2012 |
| JP | 2012-251913 | A | 12/2012 |
| JP | 2017-100039 | A | 6/2017 |

OTHER PUBLICATIONS

Kamiji et al., "Modeling and Validation of Carsickness Mechanism", SICE Annual Conference 2007, Sep. 17-20, 2007, pp. 1138-1143.

* cited by examiner

MOTION SICKNESS ESTIMATION DEVICE, MOTION SICKNESS REDUCING DEVICE AND MOTION SICKNESS ESTIMATION METHOD

CROSS-REFERENCE TO RELATED APPLICATIONS

The present application is based on PCT filing PCT/JP2020/000455, filed Jan. 9, 2020, which claims priority to JP 2019-026470, filed Feb. 18, 2019, the entire contents of each are incorporated herein by reference.

TECHNICAL FIELD

The present disclosure relates to a device and a method for estimating motion sickness an occupant of a vehicle.

BACKGROUND ART

In the modern society, a lot of time is spent on traveling on vehicles such as a car, a train, or a bus. It is expected that people's lives can be enriched by allocating these travel times to reading books, operating smartphones, or operating personal computers and by making effective use of them. However, for example, reading books while being onboard a vehicle induces motion sickness and worsens the physical condition of an occupant. As a result, effective use of the travel time cannot be achieved.

Motion sickness, also referred to as "motion disease" or "acceleration sickness", is a reaction of the autonomic nervous system that occurs when vibrations, especially irregular repetitions of acceleration and deceleration, stimulate the semicircular canals of the inner ear or the vestibule. Generally, it is said that young people or women are prone to motion sickness, but there are large individual variations due to the influence of habituation or experience with vibrations. Therefore, in order to effectively utilize the above-mentioned travel time, it is important to estimate the motion sickness level of an occupant and to control the motion of the vehicle so that the occupant does not get motion sickness.

Although the mechanism of developing motion sickness has not yet been unraveled, there is a theory that motion sickness occurs when there is a contradiction between the sensory amount of the body's equilibrium sensory information obtained by sensory organs such as the semicircular canals and an estimated amount of equilibrium sensory information estimated inside an individual on the basis of visual information, somatesthesia information, etc. (called the sensory conflict theory). There is a method of constructing a neural model based on this sensory conflict theory, estimating a sensory conflict amount from acceleration information of the head, and estimating a motion sickness level of an occupant from the sensory conflict amount that has been estimated (Patent Literature 1). As another method of estimating the sensory conflict amount from the acceleration information of the head, for example, there is a method of estimating the sensory conflict amount as a difference between the sensory amount in the gravity direction of the earth obtained from sensory organs such as semicircular canals and an estimated amount in the gravity direction that is estimated inside an individual (Non-Patent Literature 1).

CITATION LIST

Patent Literature

Patent Literature 1: JP 2012-131269 A
Non-Patent Literature 1: Kamiji, N. and other three, "Modeling and validation of carsickness mechanism", SICE Annual Conference 2007, (Japan), 2007, pp. 1138-1143.

SUMMARY OF INVENTION

Technical Problem

However, in the related art (Patent Literature 1), since the influence of habituation or experience with vibrations are not considered, the estimation accuracy of motion sickness levels decreases when the occupant is habituated to the traveling situation. That is, it is estimated that motion sickness is occurring even when no motion sickness is occurring.

The present disclosure has been made to solve the above-mentioned disadvantage, and an object of the present disclosure is to accurately estimate motion sickness even when an occupant's "habituation" with the traveling situation progresses.

Solution to Problem

A motion sickness estimation device according to the present disclosure includes: processing circuitry configured to calculate a sensory conflict amount on a basis of a motion of an occupant's head caused by vibration of a vehicle; extract a feature of a traveling situation on a basis of at least one of the motion of the occupant's head or a motion of the vehicle; determine a habituation progress state, which is a state in which the occupant's habituation to the traveling situation has progressed, on a basis of biometric information of the occupant; set sensitivity to the feature of the traveling situation on a basis of the habituation progress state; correct the sensory conflict amount on a basis of the sensitivity; and estimate a motion sickness state of the occupant on a basis of the sensory conflict amount that has been corrected.

A motion sickness estimation method according to the present disclosure includes: estimating a sensory conflict amount, which is a conflict amount between a plurality of types of sensory amounts perceived by an occupant related to a motion of the occupant's head, on the basis of the motion of the occupant's head caused by vibration of a vehicle; extracting a feature of a traveling situation related to motion sickness from the traveling situation on the basis of at least one of the motion of the occupant's head or a motion of the vehicle; determining whether or not the occupant's habituation to the traveling situation has progressed on the basis of biometric information of the occupant; setting sensitivity to the feature of the traveling situation on the basis of the habituation progress state; correcting the sensory conflict amount on the basis of the sensitivity; and estimating a motion sickness state of the occupant on the basis of the sensory conflict amount that has been corrected.

Advantageous Effects of Invention

According to a motion sickness estimation device according to the present disclosure, it is possible to accurately estimate a motion sickness level by determining the occupant's "habituation" to the traveling situation even when the occupant's habituation to the traveling situation progresses. The same applies to a motion sickness estimation method as well.

BRIEF DESCRIPTION OF DRAWINGS

FIG. 13 is also a diagram illustrating an example of the hardware configuration of the motion sickness estimation device 100 according to the embodiment of the present disclosure.

DESCRIPTION OF EMBODIMENTS

First Embodiment

Figure 1:
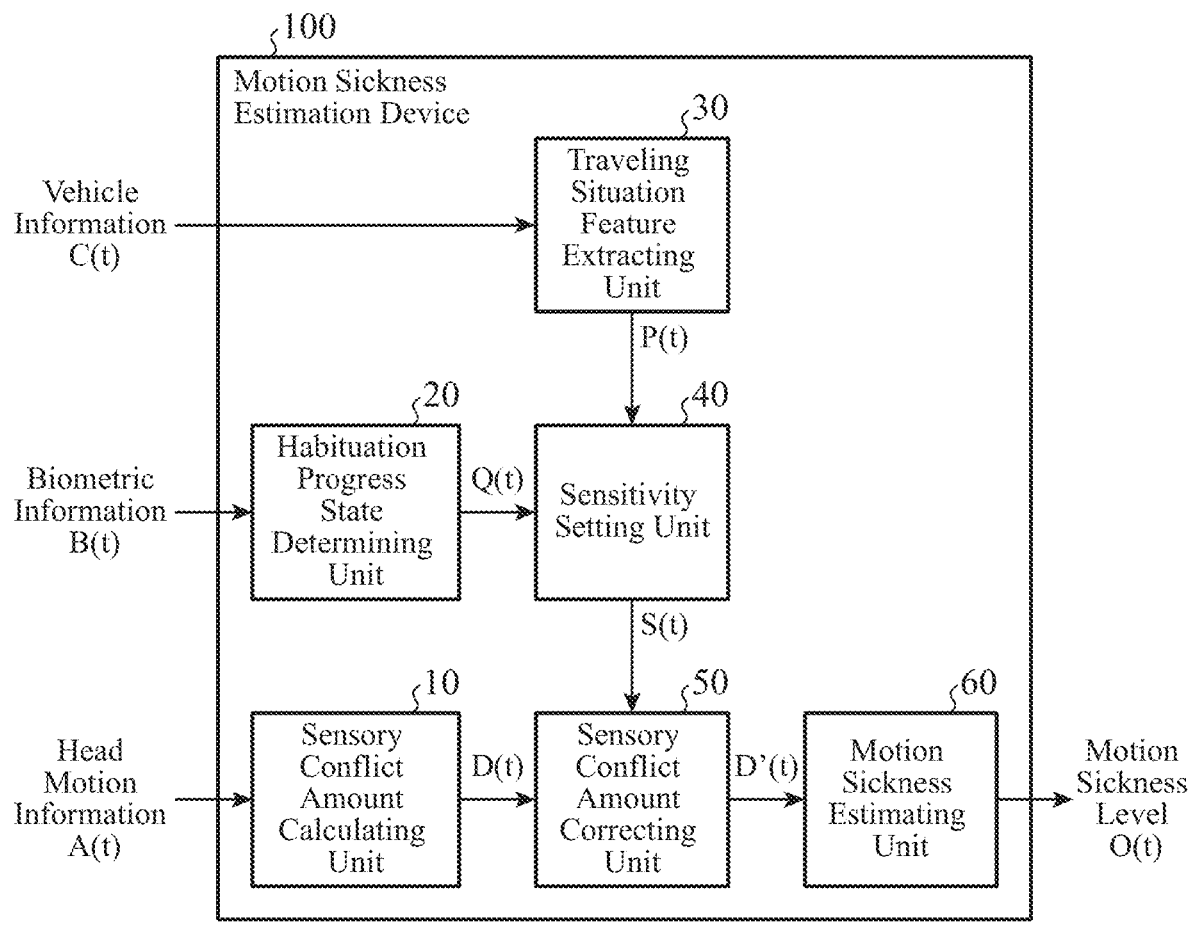
FIG. 1 is a block diagram illustrating a schematic configuration of a motion sickness estimation device according to a first embodiment of the present disclosure.

FIG. 1 is a block diagram illustrating a schematic configuration of a motion sickness estimation device 100 according to a first embodiment of the present disclosure. As illustrated in FIG. 1, the motion sickness estimation device 100 includes a sensory conflict amount calculating unit 10, a habituation progress state determining unit 20, a traveling situation feature extracting unit 30, a sensitivity setting unit 40, a sensory conflict amount correcting unit 50, and a motion sickness estimating unit 60. The motion sickness estimation device 100 receives head motion information A(t), biometric information B(t), and vehicle information C(t) as input. The sensory conflict amount calculating unit 10 receives the head motion information A(t) as input and outputs a sensory conflict amount D(t) to the sensory conflict amount correcting unit 50. The habituation progress state determining unit 20 receives the biometric information B(t) and outputs a determination result of a habituation progress state Q(t) to the sensitivity setting unit 40. The traveling situation feature extracting unit 30 receives the vehicle information C(t) and outputs a current traveling situation pattern P(t) to the sensitivity setting unit 40. The sensitivity setting unit 40 receives the determination result of the habituation progress state Q(t) and the traveling situation pattern P(t) and outputs sensitivity S(t) to the sensory conflict amount correcting unit 50. The sensory conflict amount correcting unit 50 receives the sensory conflict amount D(t) and the sensitivity S(t) and outputs a corrected sensory conflict amount D'(t) to the motion sickness estimating unit 60. The motion sickness estimating unit 60 receives the corrected sensory conflict amount D'(t) and outputs a motion sickness level O(t) of an occupant.

First, the outline of the motion sickness estimation device 100 will be described. The motion sickness estimation device 100 receives the head motion information A(t), the biometric information B(t), and the vehicle information C(t) as input. Here, variable t is a value (a positive integer) indicating the time when each piece of data has been acquired. Although the head motion information A(t) and the biometric information B(t) may be information of one occupant or may be information of a plurality of occupants, description will be given hereinafter on the assumption that the information is for one occupant for the sake of simplicity.

The head motion information A(t) is, for example, a total of six-dimensional physical quantity in which the translational acceleration (three-dimensional) of the occupant's head and the rotational angular velocity (three-dimensional) of the head are combined. The translational acceleration of the head and the rotational angular velocity of the head may be measured, for example, by attaching an acceleration sensor or a gyro sensor to the head or by embedding the above sensors in glasses or the like. Alternatively, an image of the occupant's face may be captured by using a camera or a time-of-flight (ToF) type distance sensor, and the translational acceleration and the rotational angular velocity of the head may be measured from the position or the orientation of the face in the image. It is needless to say that the method for measuring the translational acceleration and the rotational angular velocity of the head is not limited to the above and that known sensor technology may be used.

The biometric information B(t) is, for example, the heart rate, heart rate variability information, the pulse rate, pulse rate variability information, the blood pressure, respiratory information, the respiration rate, respiratory disorder, the excessive respiration rate, sweating, a change in the body temperature, or the brain wave. These pieces of information may be measured by using, for example, biosensors such as an electrocardiogram, a pulse wave meter, a respiratory meter, an electroencephalograph, a sweating sensor, or a thermosensor. Alternatively, the above biometric information may be acquired from a wristwatch-type wearable biosensor or a camera image. It is needless to say that the method for measuring the biometric information B(t) is not limited to the above and that known sensor technology may be used.

The vehicle information C(t) is, for example, the speed of the occupant's head, the acceleration of the occupant's head, the rotational angular velocity of the occupant's head, the speed of the center of gravity of the occupant's body, the acceleration of the center of gravity of the occupant's body, the rotational angular velocity around the center of gravity of the occupant's body, the vehicle speed, the acceleration of the vehicle, the rotational angular velocity of the vehicle, the accelerator amount, the brake amount, the steering angle, or the direction. Note that the rotational angular velocity of the occupant's head is information that is also used as the head motion information A(t) as described above. The vehicle information C(t) may be acquired from, for example, an electric control unit (ECU) included in the vehicle or may be acquired by attaching an acceleration sensor, a gyro sensor, or a geomagnetic sensor to the motion sickness estimation device 100. It is needless to say that the method for measuring the vehicle information C(t) is not limited to the above and that known sensor technology may be used.

The motion sickness estimation device 100 processes the head motion information A(t), the biometric information B(t), and the vehicle information C(t) and outputs a motion sickness level O(t) of the occupant. The motion sickness level O(t) represents the level of the occupant's motion sickness and is represented by a value from 0 to 1, for example. Value 0 represents a state of not being sick at all, 1 represents a state of being severely sick, and a value therebetween (for example, 0.5) is an intermediate state between 0 and 1.

The sensory conflict amount calculating unit 10 receives the head motion information A(t), which is information of the motion of the occupant's head caused by vibration of the vehicle and outputs the sensory conflict amount D(t) to the sensory conflict amount correcting unit 50. The sensory conflict amount D(t) is, for example, as in Non-Patent Literature 1, represented as a difference between a sensory amount of a sensory conflict amount in the gravity direction of the earth obtained from a sensory organ such as semicircular canals and an estimated amount of the sensory conflict amount in the gravity direction of the earth estimated inside an individual. The sensory conflict amount calculating unit 10 calculates the sensory conflict amount D(t), which is the conflict amount among a plurality of types of sensory amounts perceived by the occupant. Note that the plurality of types of sensory amounts perceived by the occupant are, for example, the sensory amount in the gravity direction of the earth obtained from a sensory organ such as semicircular canals, an estimated amount in the gravity direction of the earth obtained via the skeleton of the body, and an estimated amount in a direction obtained through the viewing angle. In addition, without being limited to the gravity direction of the earth, any one of three axial directions of the vehicle may be used such as the forward direction, the lateral direction, and the rotation direction. The method for calculating the sensory conflict amount D(t) is not limited to the above, and calculation may be performed by using known technology.

The habituation progress state determining unit 20 determines whether or not the occupant's habituation to the traveling situation is progressing on the basis of the biometric information of the occupant. A specific example is as follows. The habituation progress state determining unit 20 receives the biometric information B(t), determines the habituation progress state to the current traveling situation, and outputs the determination result of the habituation progress state Q(t) to the sensitivity setting unit 40. The determination result of the habituation progress state Q(t) is, for example, a binary value of 0 or 1. If it is determined that the habituation is not progressing, the determination result of the habituation progress state Q(t) is set to 0, and if it is determined that the habituation is progressing, the determination result of the habituation progress state Q(t) is set to 1.

The traveling situation feature extracting unit 30 extracts a feature of the traveling situation on the basis of at least one of the motion of the occupant's head and the motion of the vehicle. A specific example is as follows. The traveling situation feature extracting unit 30 receives the vehicle information C(t), analyzes time series data of the vehicle information C(t) that has been previously input, and outputs a current traveling situation pattern P(t) to the sensitivity setting unit 40. The traveling situation pattern P(t) is classified depending on, for example, the driving skills of the driver, driving preferences (control guideline in a case of an autonomous driving vehicle), the shape of the road, the traffic condition, or the weather. Alternatively, classification is made depending on simply the magnitude of the acceleration (acceleration or deceleration by the accelerator or the brake) in the front-rear direction of the vehicle, the frequency in the front-rear direction of the vehicle, the magnitude of the vehicle vibration in the gravity direction of the earth, the frequency of the vehicle vibration in the gravity direction of the earth, the magnitude of the rotational angular velocity in the roll or pitch direction, or the frequency of the rotational angular velocity in the roll or pitch direction. For example, it is suggested in Non-Patent Literature 1 that the susceptibility to motion sickness changes depending on the frequency of the rotational angular velocity, and thus it is appropriate to classify the traveling situation depending on the frequency of the rotational angular velocity. Traveling situation patterns classified by the above classification method are numbered, and the number of the traveling situation pattern that corresponds to the current traveling situation is defined as the traveling situation pattern P(t). Note that the number of types of traveling situation patterns is denoted by PN (PN is a positive integer).

The sensitivity setting unit 40 sets sensitivity to the traveling situation feature on the basis of the habituation progress state. A specific example is as follows. The sensitivity setting unit 40 receives the determination result of the habituation progress state Q(t) and the traveling situation pattern P(t), calculates the sensitivity S(t) of the sensory conflict amount to the current traveling situation, and outputs the sensitivity S(t) to the sensory conflict amount correcting unit 50. The sensitivity S(t) is, for example, any numerical value greater than or equal to 0, and a reference value is set to 1.0. Here, for example, it is defined that the sensitivity is low when the sensitivity S(t) is between 0 and 1.0 and that the sensitivity is high when the sensitivity S(t) is greater than 1.0. The initial value of the sensitivity can be set as desired. For example, the reference value 1.0 is set as the initial value. Note that the numerical value of the sensitivity is not limited to the above, and the definition may be made by a discrete value as long as a state of high sensitivity and a state of low sensitivity can be expressed.

The sensory conflict amount correcting unit 50 corrects the sensory conflict amount on the basis of the sensitivity. Specifically, the sensory conflict amount correcting unit 50 receives the sensory conflict amount D(t) and the sensitivity S(t) and outputs a corrected sensory conflict amount D'(t) to the motion sickness estimating unit 60.

The motion sickness estimating unit 60 estimates the motion sickness state of the occupant on the basis of the corrected sensory conflict amount. Specifically, the motion sickness estimating unit 60 receives the corrected sensory conflict amount D'(t) and calculates and outputs a motion sickness level O(t) of the occupant.

Next, the operation of the motion sickness estimation device 100 will be described in more detail. The sensory conflict amount calculating unit 10 receives the head motion information A(t) and outputs the sensory conflict amount D(t) to the sensory conflict amount correcting unit 50. The sensory conflict amount D(t) is calculated as a difference between a sensory amount in the gravity direction of the earth obtained from a sensory organ such as the semicircular canals and an estimated amount in the gravity direction of the earth that is estimated inside an individual.

The habituation progress state determining unit 20 receives the biometric information B(t), determines the habituation progress state to the current traveling situation, and outputs the determination result of the habituation progress state Q(t) to the sensitivity setting unit 40. The "being in a habituation progress state" is a state in which habituation to the current traveling situation is progressing and is defined as a state in which no motion sickness has developed, or mild motion sickness has developed. Note that the degree of motion sickness is determined on the basis of the subjective evaluation of the occupants. As the subjective evaluation, for example, in a case where the degree of motion sickness is classified into the following five stages by an occupant: "1: No problem at all, 2: Slightly uncomfortable, 3: Very uncomfortable, 4: Seriously uncomfortable, 5: Desire to stop immediately", stage 1 is defined as a state in which no motion sickness has developed, stage 2 is defined as mild motion sickness, and stages 3 to 5 are defined as severe motion sickness. That is, in the case of severe motion sickness, it means that the state is "not in a habituation progress state". In the determination of the habituation progress state, the state of the autonomic nervous system of the occupant is estimated from the biometric information B(t), and the habituation progress state is determined on the basis of the result. The state of the autonomic nervous system includes a normal state, parasympathetic dominance, or sympathetic dominance. Here, the parasympathetic dominance is determined as a state in which habituation is progressing. Note that the "parasympathetic dominance" means that the parasympathetic nervous system is dominant, and the "sympathetic dominance" means that the sympathetic nervous system is dominant. The parasympathetic dominance can be considered as a state in which excitement or tension is suppressed and is returning to the normal state, which is considered that mild motion sickness has developed. Conversely, the sympathetic dominance is considered that severe motion sickness has developed.

Next, the operation of estimating the state of the autonomic nervous system from the biometric information B(t) will be described. Upon estimating the state of the autonomic nervous system, first, biometric information B(t) in the normal state of an occupant is defined. The normal state is, for example, defined as the state of the autonomic nervous system of the first three minutes after the car has started. Of course, how to determine the normal state is not limited to the above, and the normal state may be determined on the basis of usual biometric information by, for example, a wristwatch-type sensor. Then, it is determined to be either in the parasympathetic dominance or the sympathetic dominance by using the change in the biometric information B(t) from the normal state. The state of the autonomic nervous system is determined, for example, on the basis of respiratory information. When the respiratory cycle is stable and the ventilation volume is reduced as compared with the normal state, it is determined to be in the parasympathetic dominance. On the other hand, when the respiratory cycle is unstable and the ventilation volume is increased as compared with the normal state, it is determined to be in the sympathetic dominance.

The traveling situation feature extracting unit 30 receives the vehicle information C(t), analyzes time series data of the vehicle information C(t) that has been previously input, and outputs a current traveling situation pattern P(t) to the sensitivity setting unit 40. The current traveling situation pattern P(t) is determined by using, as the time series data, for example vehicle information of the past for a time interval T. It is preferable that the time interval T is short from the viewpoint that the traveling situation changes every day and every minute; however, the classification accuracy drops since the amount of information is small. In view of this point, the time interval T is preferably, for example, ten minutes. In cases where the traveling situation clearly changes, such as when entering an expressway from an urban area, the traveling situation pattern may be switched immediately.

Figure 2:
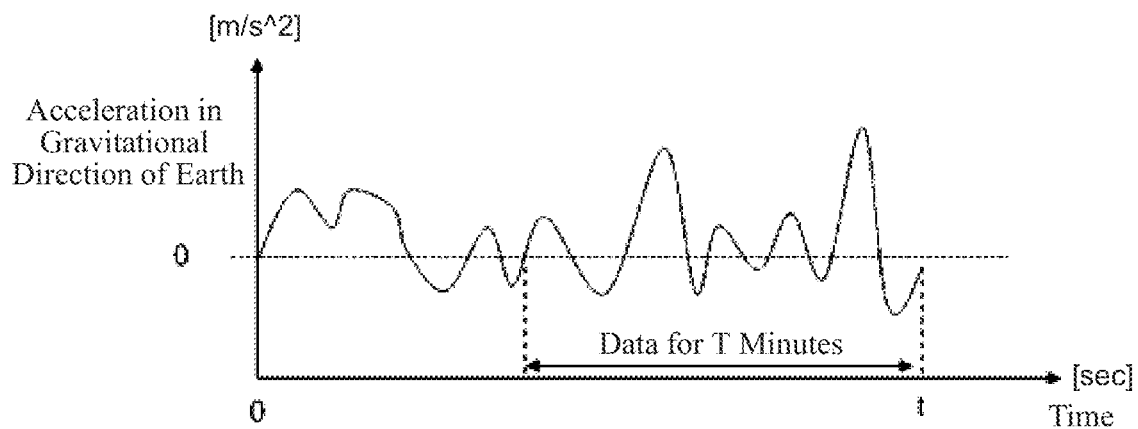
FIG. 2 is an explanatory graph illustrating a change in acceleration in the gravity direction of the earth with respect to the elapse of time in a traveling situation feature extracting unit according to the first embodiment of the present disclosure.
Figure 3:
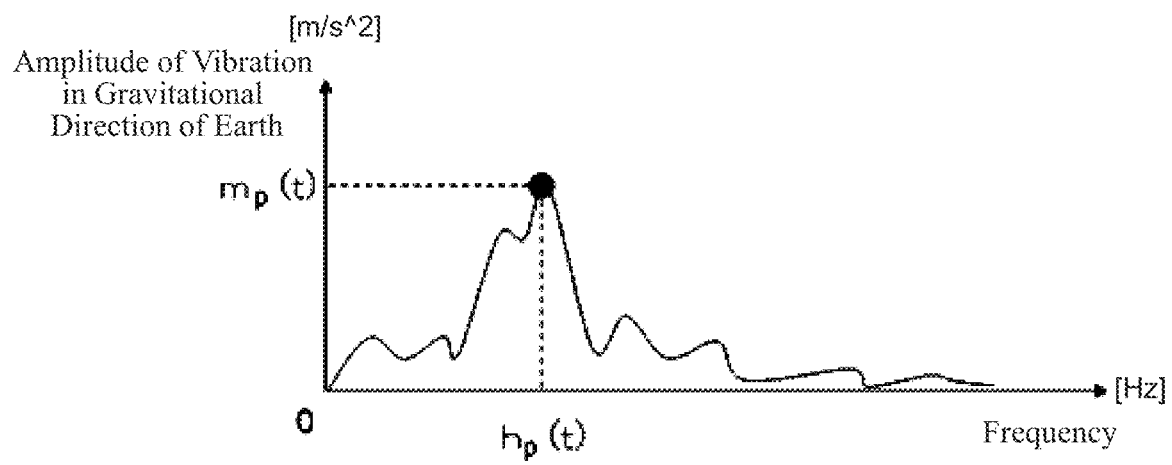
FIG. 3 is an explanatory graph illustrating a change in the amplitude of vibration in the gravity direction of the earth with respect to the change in the frequency in the traveling situation feature extracting unit according to the first embodiment of the present disclosure.

An example of the operation of determining the traveling situation pattern P(t) from the vehicle information C(t) having been input in the past will be described by referring to FIGS. 2 and 3. FIG. 2 is an explanatory graph illustrating a change in the acceleration in the gravity direction of the earth with respect to the elapse of time in the traveling situation feature extracting unit 30 according to the first embodiment of the present disclosure. FIG. 3 is an explanatory graph illustrating a change in the amplitude of a vibration component in the gravity direction of the earth with respect to the change in the frequency in the traveling situation feature extracting unit 30 according to the first embodiment of the present disclosure. In addition, FIG. 3 illustrates the frequency analysis result of past data for the time interval T [minutes].

The acceleration data in the gravity direction of the earth is used as the vehicle information C(t) having been input in the past, and the acceleration data in the gravity direction of the earth of the past is extracted for the time interval T [minutes]. The frequency spectrum is obtained by performing frequency analysis on the acceleration data that has been extracted. Known technology such as a fast Fourier transform may be applied to the frequency analysis. A peak value, which is the height of a peak of the frequency spectrum that has been obtained, is detected. In the example of FIG. 3, the main frequency of vibration is at the peak position $h_p(t)$, and the amplitude of the main frequency of vibration is at the peak value $m_p(t)$.

Figure 4:
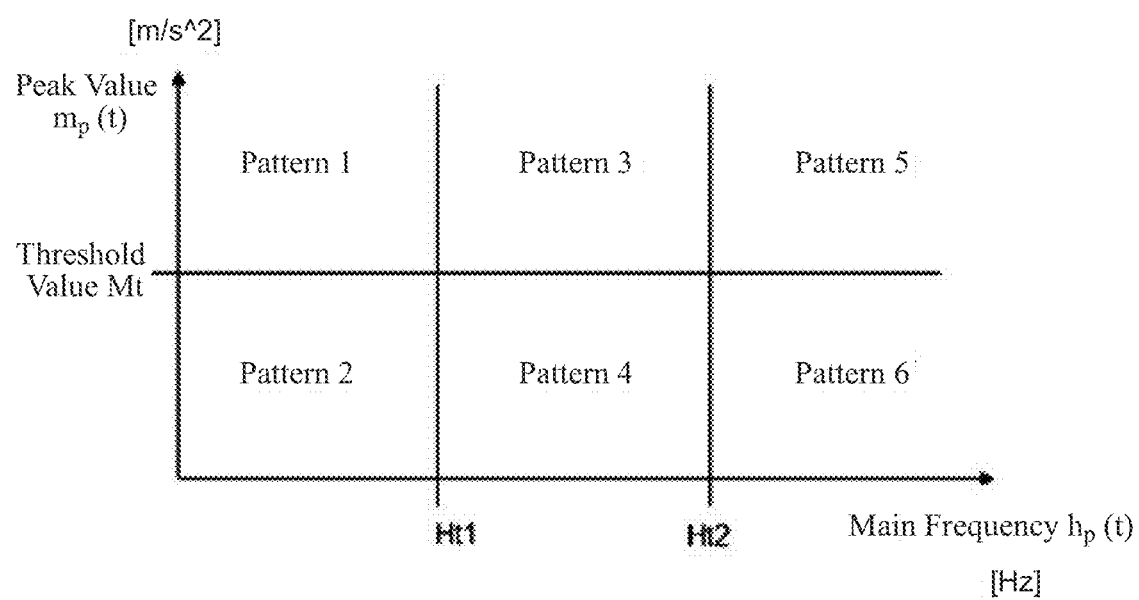
FIG. 4 is an explanatory diagram illustrating an example of determination of a traveling situation pattern in the traveling situation feature extracting unit according to the first embodiment of the present disclosure.

FIG. 4 is an explanatory diagram illustrating an example of determination of a traveling situation pattern in the traveling situation feature extracting unit 30 according to the first embodiment of the present disclosure. The susceptibility to motion sickness changes depending on the frequency characteristics such as vibration in the gravity direction of the earth and, likewise, also changes depending on the amplitude of vibration, the traveling situations are classified into patterns by using the main frequency $h_p(t)$ or the peak value $m_p(t)$ which is the amplitude of the main frequency. An example of the operation of determining a traveling situation pattern from the peak value $m_p(t)$, which is the amplitude of the main frequency of the vibration in the gravity direction of the earth that has been calculated, and the main frequency $h_p(t)$ of the vibration will be described from FIG. 4. In the description of FIG. 4, it is assumed that the value of PN as the number of types of traveling situation patterns is six.

FIG. 4 is a diagram illustrating the correspondence among the value of the main frequency $h_p(t)$ of vibration, the value of the amplitude $m_p(t)$ of the main frequency of vibration, and each traveling situation pattern. A threshold value Mt in FIG. 4 distinguishes pattern "1", pattern "3", and pattern "5" from pattern "2", pattern "4", and pattern "6" with respect to the magnitude of vibration. A threshold value Ht1 in FIG. 4 distinguishes pattern "1" and pattern "2" from pattern "3" and pattern "4" with respect to the main frequency h(t) of vibration. A threshold value Ht2 distinguishes pattern "3" and pattern "4" from pattern "5" and pattern "6" with respect to the main frequency $h_p(t)$ of vibration. Each of the threshold values is, for example, a preset fixed value. The value of the main frequency $h_p(t)$ of the vibration and the value of the amplitude $m_p(t)$ of the main frequency of the vibration that have been calculated are plotted in FIG. 4, and which traveling situation pattern corresponds to is determined.

For example, in a case where the amplitude $m_p(t)$ of the main frequency of vibration is higher than or equal to the threshold value Mt, and the main frequency $h_p(t)$ is higher than or equal to the threshold value Ht1 and smaller than the threshold value Ht2, it is determined that the traveling situation pattern P(t) is pattern "3".

As described above, the traveling situation feature extracting unit 30 classifies the traveling situation into a predetermined traveling situation pattern. Note that motion sickness is a symptom that varies greatly from person to person. For example, some occupants find it uncomfortable with large and slow vibrations, whilst other occupants find it uncomfortable with fine vibrations, and thus the traveling situation in which motion sickness is likely to occur varies. That is, there are strengths and weaknesses for each occupant with respect to the traveling situation, and there are also habituated and not-habituated traveling situations. Therefore, the traveling situations are classified into several patterns on the basis of the frequency band or the magnitude of acceleration, sensitivity is set for each of the patterns, and thereby motion sickness is estimated.

The sensitivity setting unit 40 sets sensitivity for each of the patterns. A specific example is as follows. The sensitivity setting unit 40 receives the determination result of the habituation progress state Q(t) and the traveling situation pattern P(t). The sensitivity setting unit 40 also calculates the sensitivity S(t) of the sensory conflict amount with respect to the current traveling situation and outputs the sensitivity S(t) to the sensory conflict amount correcting unit 50. When number p (p is an integer from 1 to 6) is input to the sensitivity setting unit 40 as the traveling situation pattern P(t), the sensitivity Sp(t) for number p of a traveling situation pattern updates "Sp(t)−$q_0$(t)×α", which is by Sp(t) before the input, as the sensitivity Sp(t).

Note that the coefficient $q_0$(t) is determined on the basis of the determination result of the habituation progress state Q(t). For example, if Q(t)=1 (habituation is progressing), 1.0 is set, and if Q(t)=0 (habituation is not progressing), 0.0 is set. A sensitivity amount α is the amount of sensitivity that is corrected at one time of update, and for example, a value such as 0.01 or 0.1 is set. Note that since the sensitivity S(t) is a value greater than or equal to 0 as described above, in a case where Sp(t) is smaller than 0 from the above equation, Sp(t) is set to 0. The sensitivity Sp(t) corresponding to the current traveling situation pattern p is output as the sensitivity S(t). In this manner, in a case where the habituation is progressing, the sensitivity to the corresponding traveling situation pattern is reduced, and in a case where the habituation is not progressing, the sensitivity to the corresponding traveling situation pattern is not changed, thereby making it possible to set sensitivity considering habituation to the traveling situation pattern.

The sensory conflict amount correcting unit 50 receives the sensory conflict amount D(t) and the sensitivity S(t) and outputs a corrected sensory conflict amount D'(t) to the motion sickness estimating unit 60. The corrected sensory conflict amount D'(t) is calculated by, for example, the following equation.

$$D'(t) = S(t) \times D(t) \qquad \text{Equation 1}$$

By correcting the sensory conflict amount in this manner, it is possible to calculate the conflict amount depending on the progress of habituation to the current traveling situation pattern.

The motion sickness estimating unit 60 receives the corrected sensory conflict amount D'(t) and calculates and outputs the motion sickness level O(t) of the occupant. For the calculation of the motion sickness level O(t) of the occupant from the corrected sensory conflict amount D'(t), for example, a motion sickness incidence (MSI) rate [%] is output as described in Non-Patent Literature 1, and a value obtained by normalizing the MSI value to 0 to 1 is output as the motion sickness level O(t).

Figure 5:
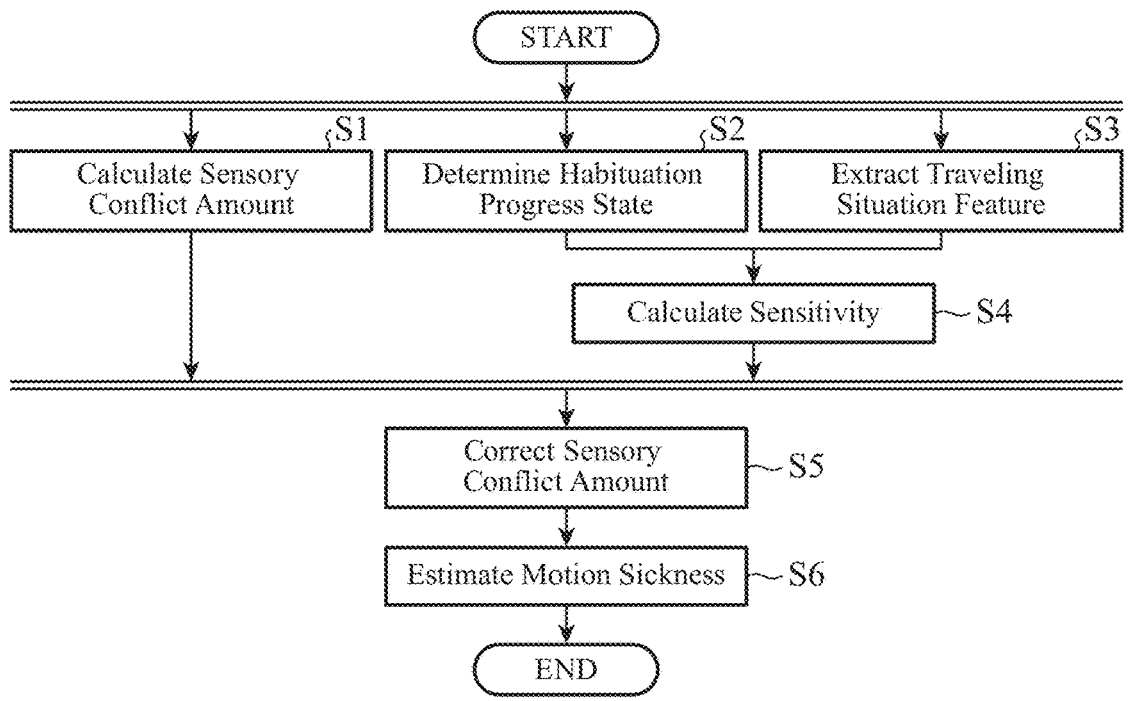
FIG. 5 is a flowchart illustrating a process of the motion sickness estimation device according to the first embodiment of the present disclosure.

Next, the procedure of the process of the motion sickness estimation device 100 according to the first embodiment will be described by referring to FIG. 5. FIG. 5 is a flowchart illustrating the process of the motion sickness estimation device 100 according to the first embodiment. The process illustrated in FIG. 5 is performed once every time the head motion information A(t), the biometric information B(t), or the vehicle information C(t) is input. First, in step S1, the sensory conflict amount calculating unit 10 calculates the sensory conflict amount D(t) from the head motion information A(t) and outputs the sensory conflict amount D(t) to the sensory conflict amount correcting unit 50.

Next, in step S2, the habituation progress state determining unit 20 determines the habituation progress state with respect to the current traveling situation from the biometric information B(t) and outputs the determination result of the habituation progress state Q(t) to the sensitivity setting unit 40.

Next, in step S3, the traveling situation feature extracting unit 30 analyzes time series data of C(t) and outputs the current traveling situation pattern P(t) to the sensitivity setting unit 40.

Next, in step S4, the sensitivity setting unit 40 calculates the sensitivity S(t) of the sensory conflict amount with respect to the current traveling situation from the determination result of the habituation progress state Q(t) and the traveling situation pattern P(t) and outputs to the sensory conflict amount correcting unit 50.

Next, in step S5, the sensory conflict amount correcting unit 50 outputs a corrected sensory conflict amount D'(t) that has been corrected on the basis of the sensory conflict amount D(t) and the sensitivity S(t) to the motion sickness estimating unit 60.

Next, in step S6, the motion sickness estimating unit 60 calculates and outputs the motion sickness level O(t) of the occupant from the corrected sensory conflict amount D'(t).

By correcting the sensory conflict amount D(t) as described above and setting it as the sensory conflict amount D'(t), it is possible to calculate a conflict amount depending on the progress of habituation to the current traveling situation pattern.

The motion sickness estimation device 100 includes the sensory conflict amount calculating unit 10, the habituation progress state determining unit 20, the traveling situation feature extracting unit 30, the sensitivity setting unit 40, the sensory conflict amount correcting unit 50, and the motion sickness estimating unit 60 and corrects the sensory conflict amount by setting sensitivity in consideration of habituation to the traveling situation pattern by reducing the sensitivity to the corresponding traveling situation pattern in a case where the habituation is progressing and not changing the sensitivity to the corresponding traveling situation pattern in a case where the habituation is not progressing from the determination result of the habituation progress state Q(t) determined by the habituation progress state determining unit 20 and the traveling situation pattern P(t) determined by the traveling situation feature extracting unit 30.

In the motion sickness estimation device according to the first embodiment, the motion sickness state can be accurately determined even when habituation to the traveling situation occurs, by correcting the sensory conflict amount depending on the habituation progress state to the traveling situation.

Furthermore, the habituation progress state determining unit 20 in the motion sickness estimation device 100 estimates the state of the occupant's autonomic nervous system from the biometric information B(t) and determines the habituation progress state on the basis of the result. As described above, in the motion sickness estimation device according to the first embodiment, the habituation progress state can be accurately determined depending on the internal state of the occupant by determining the habituation progress state on the basis of the state of the autonomic nervous system.

Furthermore, in the motion sickness estimation device according to the first embodiment, it is possible to accurately estimate a motion sickness level by determining the occupant's "habituation" to the traveling situation even when the occupant's habituation to the traveling situation progresses.

Note that although respiratory information is used for estimation of the state of the autonomic nervous system in the first embodiment, it is not limited thereto. For example, the state of the autonomic nervous system may be estimated by using heart rate variability information. As a method for estimating the state of the autonomic nervous system by using heart rate variability information, frequency analysis is performed on time-series data of heart rate intervals, and the state of the autonomic nervous system is estimated from the ratio between high-frequency components attributable to respiration (0.15 to 4.0 [Hz]) and low-frequency components attributable to, for example, blood pressure variability (0.04 to 0.15 [Hz]). In addition, in the respiratory information, the state of the autonomic nervous system may be estimated by using an index other than the stability of the respiratory cycle and the ventilation volume.

Note that, in the first embodiment, the traveling situation pattern is determined from the magnitude and the main frequency of vibration in the gravity direction of the earth; however, it is not limited thereto. A vehicle operation amount of the accelerator amount or the brake amount may be used, or the traveling situation pattern may be determined by using the rotational angular velocity, the geomagnetic information, the weather information, or the traveling route information.

Note that, in the first embodiment, the motion sickness level is estimated on the basis of the corrected sensory conflict amount; however, it is not limited thereto. For example, the motion sickness level may be estimated using the state of the autonomic nervous system, or the motion sickness level may be estimated to be high when the state of the autonomic nervous system is in sympathetic dominance.

Note that, in the first embodiment, the threshold values for classifying the traveling situation pattern are fixed values; however, it is not limited thereto. For example, determination may be automatically made using a learning method such as self-organizing maps (SOM) or the k-nearest neighbors algorithm. The "self-organizing maps (SOM)" is an unsupervised learning neural network of a two-layer structure that can map input data to a desired dimension by unsupervised learning. The "k-nearest neighbors algorithm" is a learning method of estimating a class to which data belongs by a majority decision, by acquiring any k pieces of data in order of closer distance from the unknown data among training data plotted in a vector space when unknown data is obtained.

Note that, in the first embodiment, the traveling situation feature extracting unit 30 classifies the current traveling situation into predetermined patterns, and the sensitivity setting unit 40 sets sensitivity for each of the patterns; however, it is not limited thereto. For example, a function may be set in which the sensitivity continuously changes depending on the main frequency of vibration or the amplitude of vibration representing the traveling situation. However, such a function is non-linear and complex, and it is difficult to select a function or a parameter. Therefore, as described in the first embodiment, the traveling situations are classified into patterns, and sensitivity is set for each of the patterns.

Second Embodiment

Figure 6:
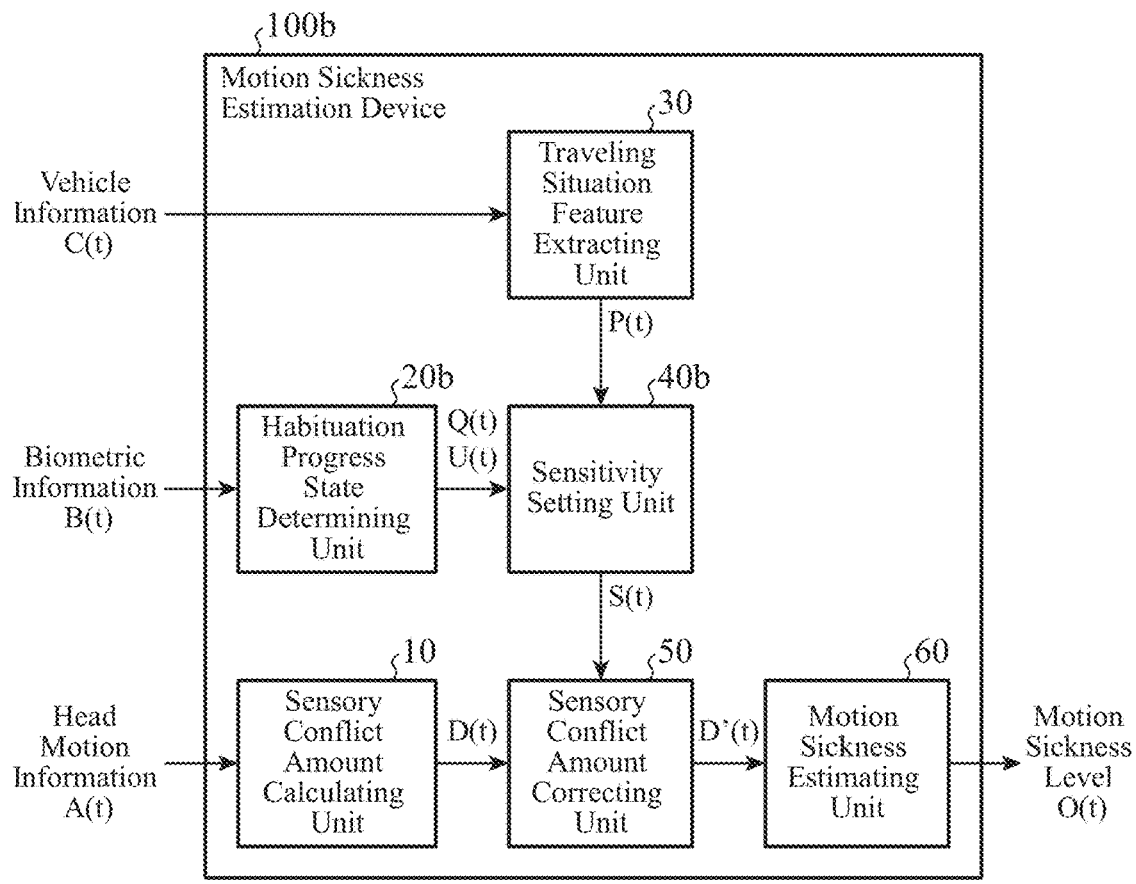
FIG. 6 is a block diagram illustrating a schematic configuration of a motion sickness estimation device according to a second embodiment of the present disclosure.

FIG. 6 is a block diagram illustrating a schematic configuration of a motion sickness estimation device 100b according to a second embodiment of the present disclosure. The motion sickness estimation device 100b illustrated in FIG. 6 includes the motion sickness estimation device 100b instead of the motion sickness estimation device 100 illustrated in FIG. 1. The motion sickness estimation device 100b is different in that it includes a habituation progress state determining unit 20b instead of the habituation progress state determining unit 20 and a sensitivity setting unit 40b instead of the sensitivity setting unit 40. In FIG. 6, the same or a corresponding component as that illustrated in FIG. 1 is denoted by the same symbol as that in FIG. 1. Meanwhile, description of the same or a corresponding component as or to that illustrated in FIG. 1 will be omitted.

The difference from the first embodiment is that the habituation progress state determining unit 20b outputs a determination result of the habituation progress state Q(t) and an autonomic nervous system state U(t) to the sensitivity setting unit 40b and that the sensitivity setting unit 40b sets the sensitivity on the basis of the determination result of the habituation progress state Q(t) and the autonomic nervous system state U(t).

The habituation progress state determining unit 20b receives biometric information B(t) and outputs the determination result of the habituation progress state Q(t) and the autonomic nervous system state U(t) to the sensitivity setting unit 40b. The habituation progress state determining unit 20b sets, for example, the autonomic nervous system state U(t) to 0 if the autonomic nervous system state is in the normal state, sets the autonomic nervous system state U(t) to 1 if the autonomic nervous system is in parasympathetic dominance, and sets the autonomic nervous system state U(t) to 2 if the autonomic nervous system is in sympathetic dominance.

The sensitivity setting unit 40b receives the determination result of the habituation progress state Q(t), the autonomic nervous system state U(t), and the traveling situation pattern P(t), calculates the sensitivity S(t) for the current traveling situation pattern, and outputs the sensitivity S(t) to the sensory conflict amount correcting unit 50.

In the first embodiment, the sensitivity setting unit 40b corrects the sensitivity so that the sensitivity to the sensory conflict amount becomes smaller in a case where the occupant has developed mild motion sickness and is habituated to the traveling situation pattern. In the second embodiment, in addition to the above-mentioned correction of sensitivity, in a case where the occupant has developed severe motion sickness, the sensitivity is corrected so as to be highly sensitive to the sensory conflict amount. When number p is input to the sensitivity setting unit 40b as the traveling situation pattern P(t), the sensitivity Sp(t) for number p of a traveling situation pattern updates "Sp(t)−$q_0$(t)×α", which is by Sp(t) before the input, as the sensitivity Sp(t).

Here, the coefficient $q_0$(t) is determined on the basis of the determination result of the habituation progress state Q(t) and the autonomic nervous system state U(t). For example, where Q(t)=1 and U(t)=1 (the state in which habituation is progressing), 1.0 is set, and where Q(t)=0 and U(t)=0 (the state in which habituation is not progressing and the state in which no severe motion sickness is developed), 0.0 is set. Where Q(t)=0 and U(t)=2 (the state in which habituation is not progressing and the state in which severe motion sickness is developed), −1.0 is set. By updating the sensitivity in this manner, in a case where severe motion sickness has developed, that is, in a case of sympathetic dominance, correcting the sensitivity to the sensory conflict amount to be higher allows the motion sickness level O(t) to become likely to have a high value. Note that the coefficient $q_0$(t) is not limited to the above values, and any value may be set.

The motion sickness estimation device 100b includes the sensory conflict amount calculating unit 10, the habituation progress state determining unit 20b, the traveling situation feature extracting unit 30, the sensitivity setting unit 40b, the sensory conflict amount correcting unit 50, and the motion sickness estimating unit 60 and calculates the motion sickness level O(t) of the occupant so that the sensitivity for the sensory conflict amount is corrected to be higher in a case where severe motion sickness is developed, that is, in a case of sympathetic dominance, from the determination result of the habituation progress state Q(t) and the autonomic nervous system state U(t) output from the habituation progress state determining unit 20 and the traveling situation pattern P(t) determined by the traveling situation feature extracting unit 30.

In the motion sickness estimation device according to the second embodiment, the motion sickness level can be estimated accurately by correcting the sensitivity for the sensory conflict amount to be high when severe motion sickness is developed.

Third Embodiment

Figure 7:
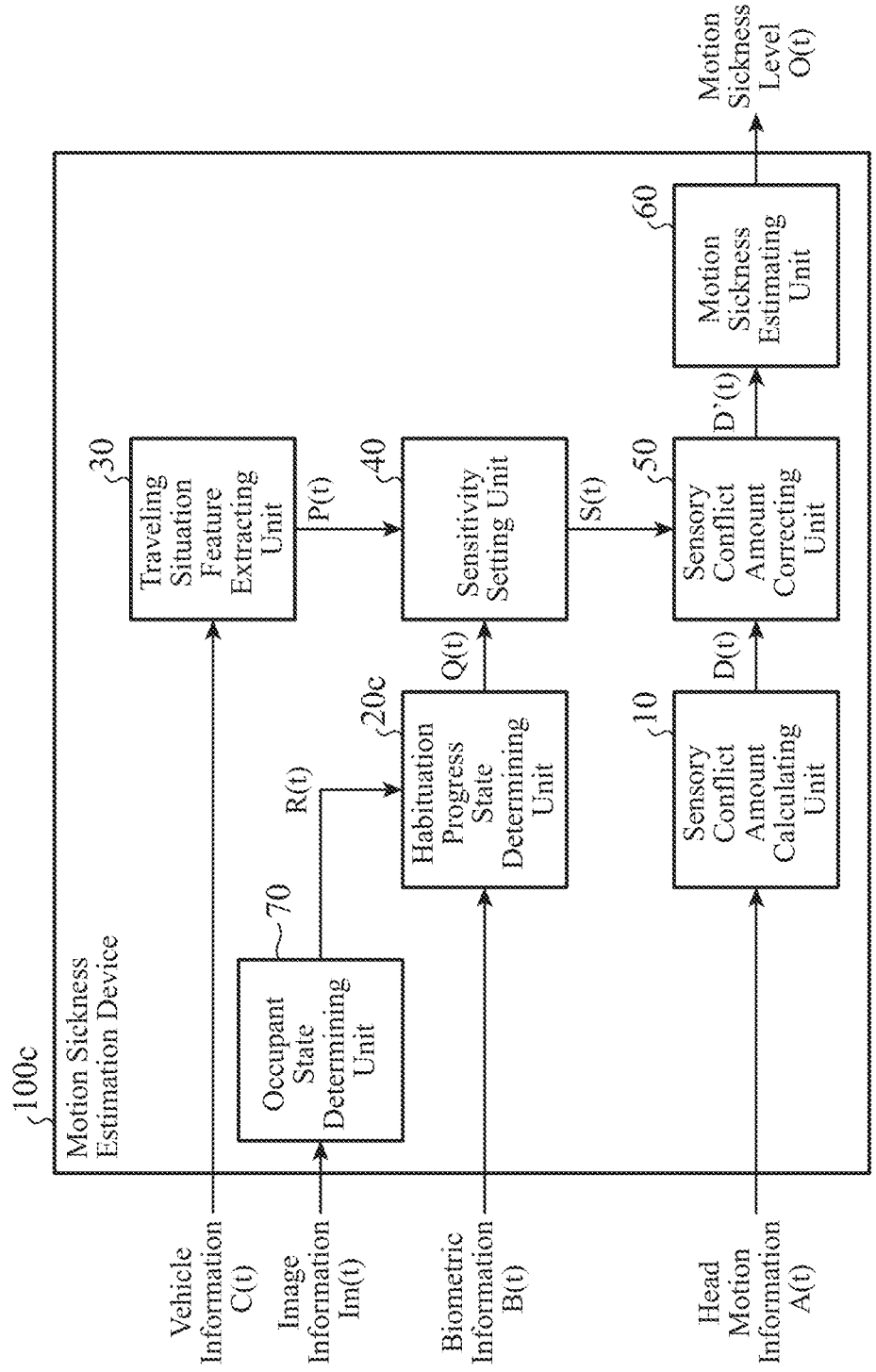
FIG. 7 is a block diagram illustrating a schematic configuration of a motion sickness estimation device according to a third embodiment of the present disclosure.

FIG. 7 is a block diagram illustrating a schematic configuration of a motion sickness estimation device 100c according to a third embodiment of the present disclosure. The motion sickness estimation device 100c illustrated in FIG. 7 includes the motion sickness estimation device 100c instead of the motion sickness estimation device 100 illustrated in FIG. 1. The motion sickness estimation device 100c is different in that it further includes an occupant state determining unit 70 and includes a habituation progress state determining unit 20c instead of the habituation progress state determining unit 20. In FIG. 7, the same or a corresponding component as that illustrated in FIG. 1 is denoted by the same symbol as that in FIG. 1. Meanwhile, description of the same or a corresponding component as or to that illustrated in FIG. 1 will be omitted.

The difference from the first embodiment is that the habituation progress state is determined on the basis of a determination result of an occupant state when the habituation progress state to the traveling situation is determined.

The occupant state determining unit 70 receives image information Im(t) and outputs occupant state information R(t) to the habituation progress state determining unit 20c. The image information Im(t) is image information (captured images) of a series of frames showing a moving image of a space in which the space including an occupant is imaged at a predetermined frame rate. For example, the occupant state information R(t) imaged at a frame rate of 30 [FPS] is information indicating the occupant state not related to motion sickness, and includes information of the awakening level, the stress level, or the fatigue level of the occupant. The level of each occupant state described above is defined by, for example, a value from 0 to 1. Regarding the awakening level, level 0 is defined as a not awakened state, and level 1 is defined as an awakened state. As for the stress level, level 0 is defined as a state free from stress, and level 1 is defined as a state under a great stress. As for the fatigue level, level 0 can be defined as a state free from fatigue, and level 1 can be defined as a state with fatigue.

The habituation progress state determining unit 20c determines the habituation progress state to the current traveling situation on the basis of the biometric information B(t) and the occupant state information R(t).

Figure 8:
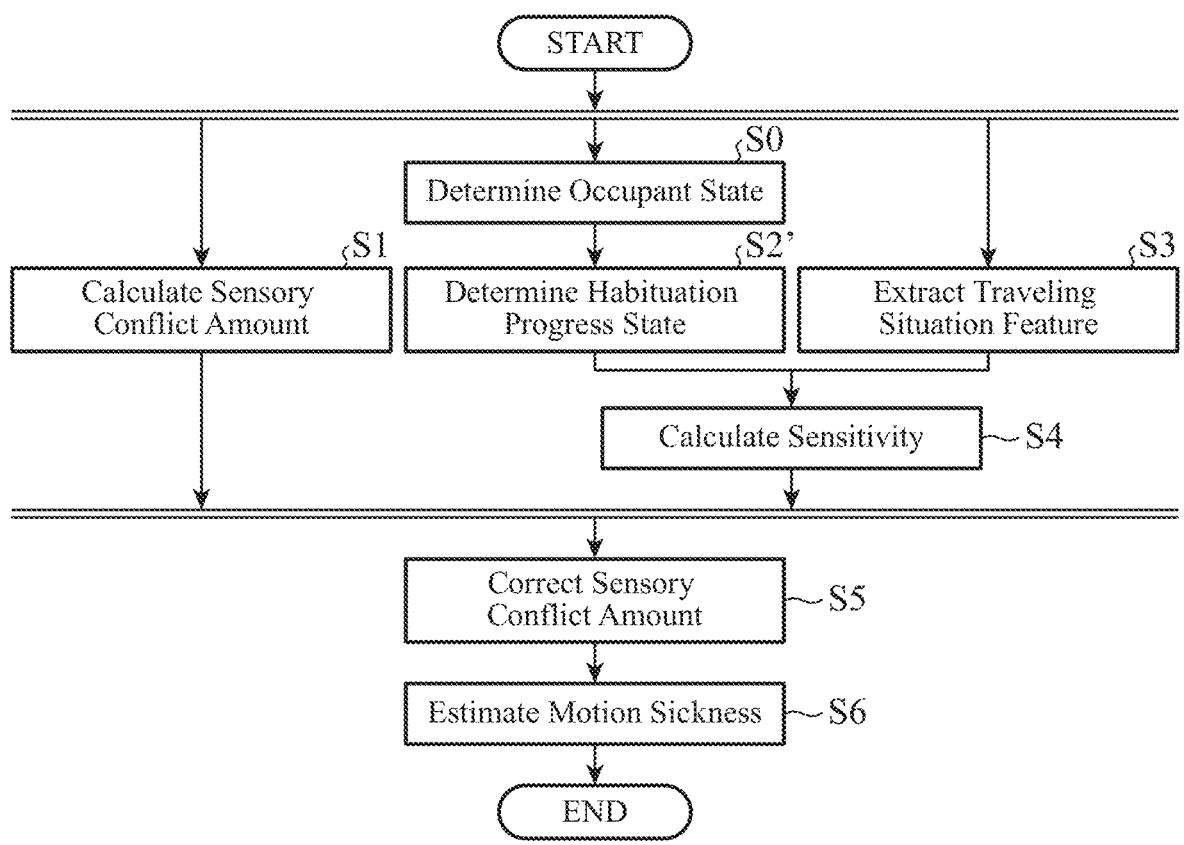
FIG. 8 is a flowchart illustrating a process of the motion sickness estimation device according to the third embodiment of the present disclosure.

Next, the procedure of the process of the motion sickness estimation device 100c will be described by referring to FIG. 8. FIG. 8 is a flowchart illustrating the process of the motion sickness estimation device 100c according to the third embodiment. The flowchart illustrated in FIG. 8 is different from the flowchart illustrated in FIG. 5 in that it includes step 0, which is a step of determining the state of an occupant, and includes step S2', which is a step of determining the habituation progress state, instead of step S2 which is a step of determining the habituation progress state. In FIG. 8, the same or a corresponding step as that illustrated in FIG. 5 is denoted by the same symbol as that in FIG. 5. Meanwhile, description of the same or a corresponding step as or to that illustrated in FIG. 5 will be omitted.

First, in step S0, the occupant state determining unit 70 calculates occupant state information R(t) from image information Im(t). In the following, the occupant state information will be described as the awakening level of the occupant. The awakening level of an occupant can be calculated from time series data of image information. For example, the awakening level of the occupant can be calculated by detecting the open or closed state of the occupant's eyes from the image information Im(t) and calculating an index such as PERCLOS (ratio of eye-closing time in a predetermined period of time). The method for calculating the awakening level is not limited to the above and may be calculated using known technology.

Next, in step S2', the habituation progress state determining unit 20c determines the habituation progress state to the current traveling situation on the basis of the biometric information B(t) and the occupant state information R(t). In the first embodiment, parasympathetic dominance is determined to be a habituation progress state; however, the parasympathetic dominance is observed not only when a mild sickness is occurring but also when the awakening level decreases. Therefore, the habituation progress state determining unit 20c determines the habituation progress state in consideration of whether the parasympathetic dominance is due to occurrence of mild sickness or a decrease in the awakening level. Specifically, a state of parasympathetic dominance and a high awakening level is determined as the habituation progress state. In determining whether the awakening level is high or low, a threshold value is set for the awakening level, and the awakening level is determined to be high if the awakening level is greater than or equal to the threshold value and is determined to be low if the awakening level is below the threshold value.

As a criterion other than PERCLOS for determination as to whether the awakening level is high or low, for example, the awakening level is classified into five stages: "1: Not sleepy at all, 2: Slightly sleepy, 3: Sleepy, 4: Very sleepy, 5: Extremely sleepy", and define that the awakening level is high for stage 3 or higher and that the awakening level is low for lower stages, which is used as the "facial expression evaluation criteria".

In order to determine a threshold value for PERCLOS, conduct an experiment in advance and obtain the correspondence between the above facial expression evaluation criteria and values of PERCLOS. To "obtain the correspondence" means to find which stage of the facial expression evaluation criteria a value of PERCLOS corresponds to. The correspondence between the facial expression evaluation criteria and PERCLOS is obtained from the experiment, and a value of PERCLOS that corresponds to the distinguishing point between stages 3 and higher and lower stages of the facial expression evaluation criteria is obtained. The value of PERLCOS that corresponds to this distinguishing point is used as a threshold value set for determination as to whether the awakening level is high or low.

The motion sickness estimation device 100c includes the sensory conflict amount calculating unit 10, the habituation progress state determining unit 20c, the traveling situation feature extracting unit 30, the sensitivity setting unit 40, the sensory conflict amount correcting unit 50, the motion sickness estimating unit 60, and the occupant state determining unit 70 and outputs the determination result of the habituation progress state Q(t) determined on the basis of the biometric information B(t) and the occupant state information R(t), corrects the sensory conflict amount from the determination result of the habituation progress state Q(t) and the traveling situation pattern P(t), and thereby calculates the motion sickness level O(t) of the occupant.

In the third embodiment, by determining the habituation progress state in consideration of the occupant state information, it is possible to suppress the cases where it is determined that habituation is progressing even though habituation is not progressing, thereby enabling accurate determination of the habituation progress state. As a result, the motion sickness level can be estimated accurately.

Note that, in the third embodiment, the awakening level is estimated using the image information; however, it is not limited thereto. For example, the awakening level may be estimated on the basis of biometric information, or the awakening level may be estimated from an operation history of a smart phone or the like.

Note that, in the third embodiment, the habituation progress state is determined on the basis of the awakening level; however, it is not limited thereto. As described above, the habituation progress state may be determined on the basis of the stress level or the fatigue level.

Note that, in the third embodiment, the motion sickness level is estimated on the basis of the corrected sensory conflict amount; however, it is not limited thereto. For example, the motion sickness level may be estimated using the state of the autonomic nervous system, or the motion sickness level may be estimated to be high when the state of the autonomic nervous system is in sympathetic dominance, thereby setting a higher sensitivity to the traveling situation pattern. Alternatively, the motion sickness level may be estimated on the basis of the occupant state information. For example, in a case where the awakening level is lowered as the occupant state information, it can be determined that the occupant is asleep, and thus the motion sickness level is estimated to be small. That is, the motion sickness estimation device 100c may estimate the motion sickness state on the basis of the state of the autonomic nervous system in addition to the corrected sensory conflict amount. Furthermore, the motion sickness estimation device 100c may estimate the motion sickness state on the basis of the occupant state in addition to the sensory conflict amount and the state of the autonomic nervous system.

Fourth Embodiment

Figure 9:
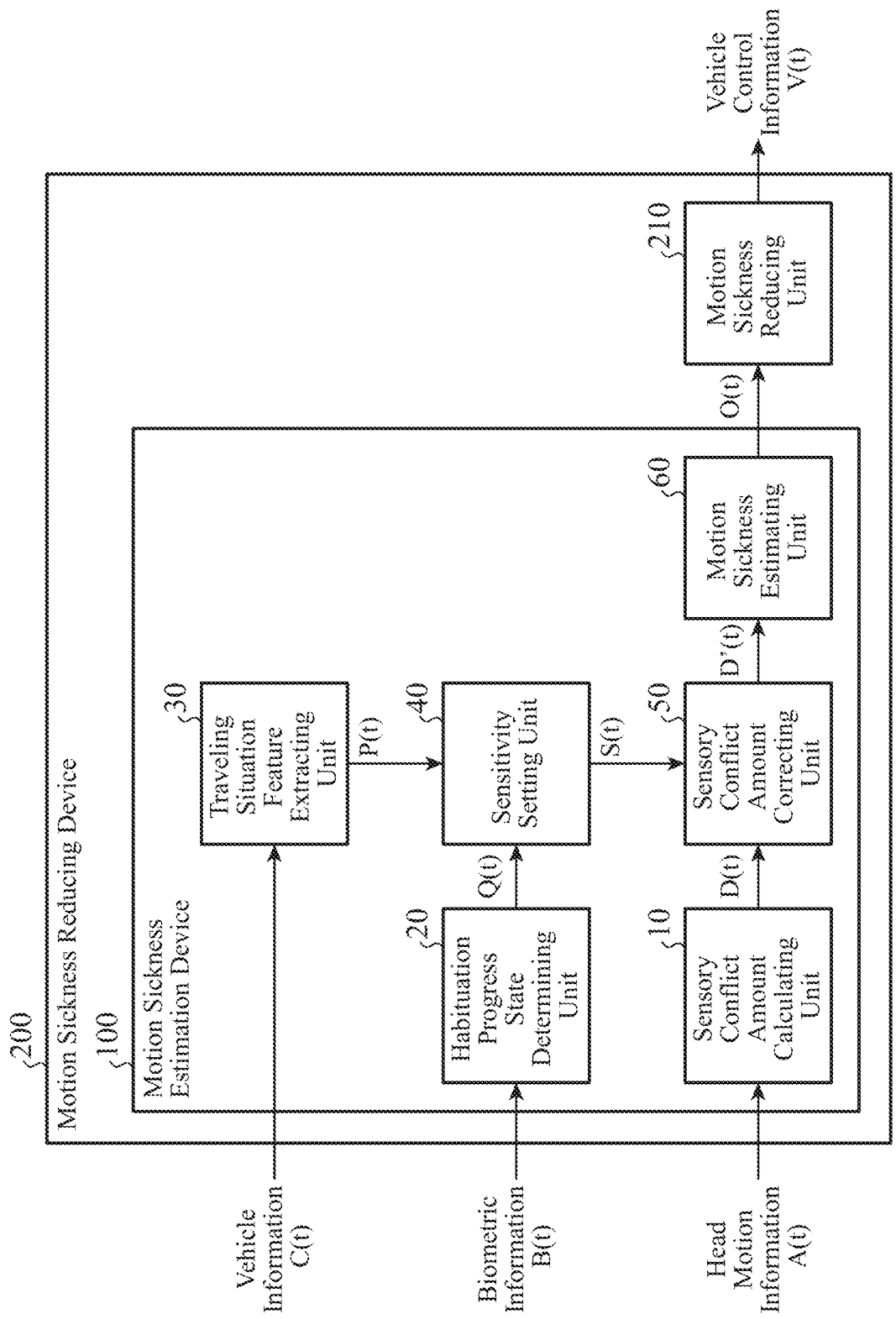
FIG. 9 is a block diagram illustrating a schematic configuration of a motion sickness reducing device according to a fourth embodiment of the present disclosure.

FIG. 9 is a block diagram illustrating a schematic configuration of a motion sickness reducing device according to a fourth embodiment of the present disclosure. A motion sickness reducing device 200 illustrated in FIG. 9 includes a motion sickness reducing unit 210 in addition to the motion sickness estimation device 100 illustrated in FIG. 1. In FIG. 9, the same or a corresponding component as that illustrated in FIG. 1 is denoted by the same symbol as that in FIG. 1. Meanwhile, description of the same or a corresponding component as or to that illustrated in FIG. 1 will be omitted.

The motion sickness reducing unit 210 receives the motion sickness level O(t) from the motion sickness estimation device 100 and outputs vehicle control information V(t) that reduces the motion sickness of the occupant. The vehicle control information V(t) is, for example, a target locus, a target speed, or a target steering angle of traveling of the vehicle in a case where the vehicle is an autonomous driving vehicle. The above-mentioned value is set in the vehicle control information V(t) so that the motion sickness level decreases when the motion sickness level is high. Specifically, the values of the target locus, the target speed, or the target steering angle are set so that the vibration or acceleration or deceleration during traveling is reduced. Alternatively, the vehicle control information V(t) is, for example, warning information for prompting a driver to avoid sudden acceleration, sudden braking, and sudden steering in a case where the vehicle is manually driven by the driver. Note that for the motion sickness level to be high means that the motion sickness level is higher than a predetermined threshold value.

According to the motion sickness reducing device of the fourth embodiment, it is possible to suppress motion sickness of an occupant by outputting vehicle control information so that the motion sickness level is lowered when the motion sickness level becomes high.

Fifth Embodiment

Figure 10:
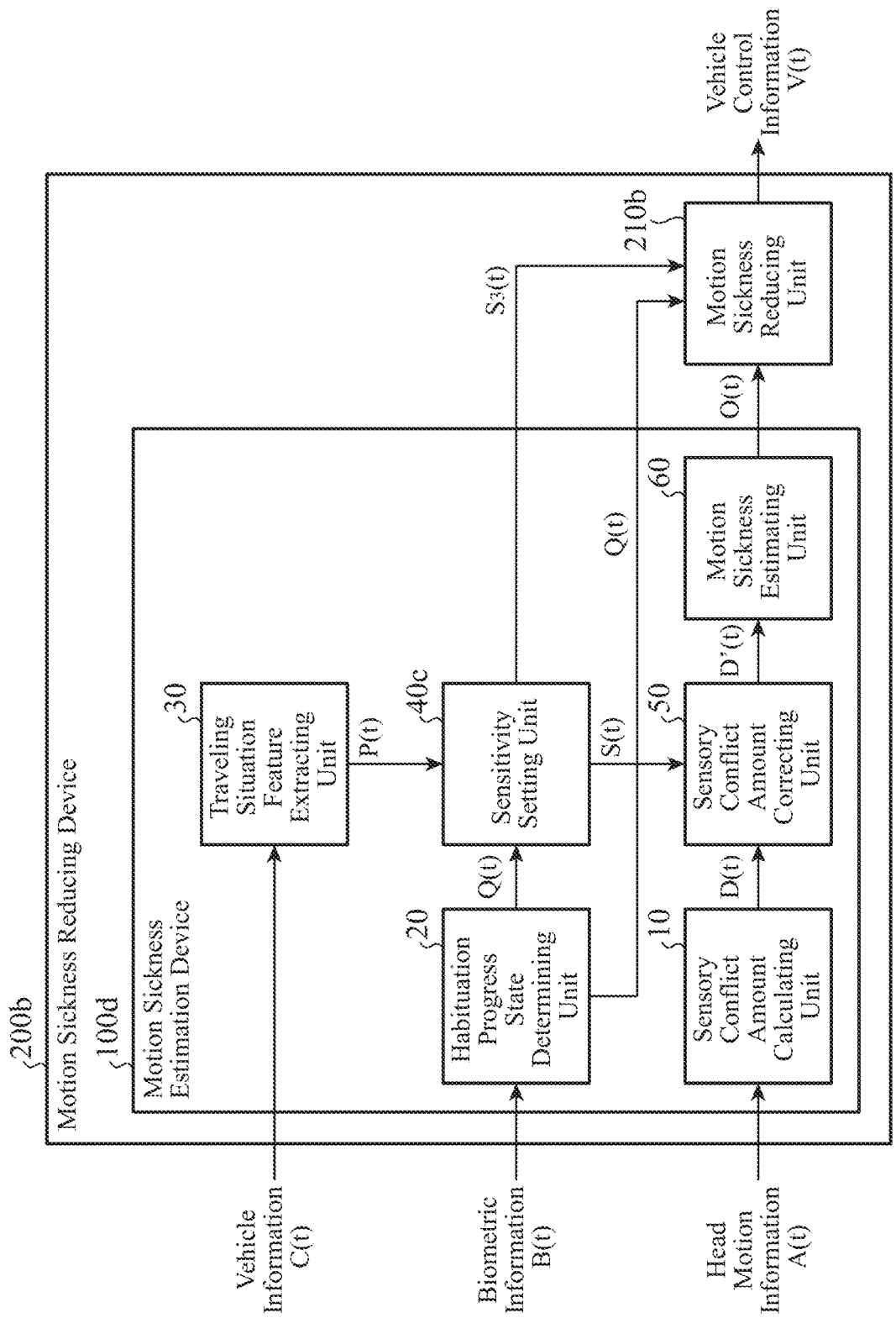
FIG. 10 is a block diagram illustrating a schematic configuration of a motion sickness reducing device according to a fifth embodiment of the present disclosure.

FIG. 10 is a block diagram illustrating a schematic configuration of a motion sickness reducing device according to a fifth embodiment of the present disclosure. A motion sickness reducing device 200b illustrated in FIG. 10 is different from the motion sickness reducing device 200 illustrated in FIG. 9 in that it includes a sensitivity setting unit 40c instead of the sensitivity setting unit 40, includes a motion sickness estimation device 100d instead of the motion sickness estimation device 100, and includes a motion sickness reducing unit 210b instead of the motion sickness reducing unit 210. In FIG. 10, the same or a corresponding component as that illustrated in FIG. 9 is denoted by the same symbol as that in FIG. 9. Meanwhile, description of the same or a corresponding component as or to that illustrated in FIG. 9 will be omitted.

The sensitivity setting unit 40c receives a determination result of the habituation progress state Q(t) and a traveling situation pattern P(t), calculates the sensitivity S(t) of a sensory conflict amount with respect to the current traveling situation, outputs the sensitivity S(t) to the sensory conflict amount correcting unit 50, and outputs sensitivities $S_{all}(t)$ of the sensory conflict amount with respect to all traveling situation patterns to the motion sickness reducing unit 210b. As for $S_{all}(t)$, for example, in a case where there are PN types of traveling situation patterns, PN types of sensitivities $S_1(t)$ to $S_{PN}(t)$ are output as $S_{all}$.

The motion sickness estimation device 100d receives head motion information A(t), biometric information B(t), and vehicle information C(t) as input and outputs, to the motion sickness reducing unit 210b, the determination result of the habituation progress state Q(t), the motion sickness level O(t), and the sensitivities $S_{all}(t)$ of the sensory conflict amount with respect to all traveling situation patterns.

The motion sickness reducing unit 210b receives the determination result of the habituation progress state Q(t), the motion sickness level O(t), and the sensitivities $S_{all}(t)$ of the sensory conflict amount with respect to all traveling situation patterns as input and outputs vehicle control information V(t).

The motion sickness reducing unit 210b is the same as in the fourth embodiment in that it outputs vehicle control information V(t) so that the motion sickness level decreases when the motion sickness level increases. In addition, the motion sickness reducing unit 210b generates and outputs vehicle control information V(t) so that the occupant's habituation to the traveling situation progresses on the basis of the determination result of habituation progress state.

The configuration of the present embodiment is to obtain whether the sensitivity to a traveling situation pattern is high or low and whether or not habituation to the traveling situation pattern is progressing. A traveling situation pattern of a high sensitivity refers to a traveling situation pattern in which the occupant is prone to motion sickness, that is, a traveling situation pattern that the occupant finds it uncomfortable. One of the vehicle control methods is to control to avoid such a traveling situation pattern of a high sensitivity; however, if such control is continued, the occupant has no chance of getting habituated to the traveling situation pattern that the occupant finds it uncomfortable. In order to generate vehicle control information V(t) so that habituation to a traveling situation pattern that the occupant finds it uncomfortable progresses and that traveling situation patterns that the occupant finds it uncomfortable are eliminated, that is, so that the occupant becomes habituated to the traveling situation, for example, control is performed so that a traveling situation pattern of a high sensitivity and a traveling situation pattern of a low sensitivity are repeated alternately. By controlling the vehicle so as to have a traveling situation pattern of a highly sensitive and maintaining a state of mild motion sickness, that is, a habituation progress state, the sensitivity to the traveling situation pattern can be lowered, and the occupant can overcome the traveling situation pattern that the occupant finds it uncomfortable. However, there are cases where the determination result of the habituation progress state Q(t) transits to a state that is not the "habituation progress state" before the sensitivity sufficiently decreases. In that case, the vehicle is controlled so as to have a traveling situation pattern of a low sensitivity, that is, a traveling situation pattern that the occupant does not find it uncomfortable, and thereby preventing the motion sickness level from becoming high. By controlling the vehicle in this manner, it is possible to allow the occupant to get habituated to a traveling situation pattern that the occupant finds it uncomfortable and to let the occupant experience the traveling situation pattern of a high sensitivity. Note that patterns of a high sensitivity and patterns of a low sensitivity can be obtained by referring to the sensitivities Sail of the sensory conflict amount with respect to all the traveling situation patterns.

According to the motion sickness reducing device according to the fifth embodiment, motion sickness of an occupant can be reduced by controlling the vehicle so that the occupant's habituation to the traveling situation progresses.

Sixth Embodiment

Figure 11:
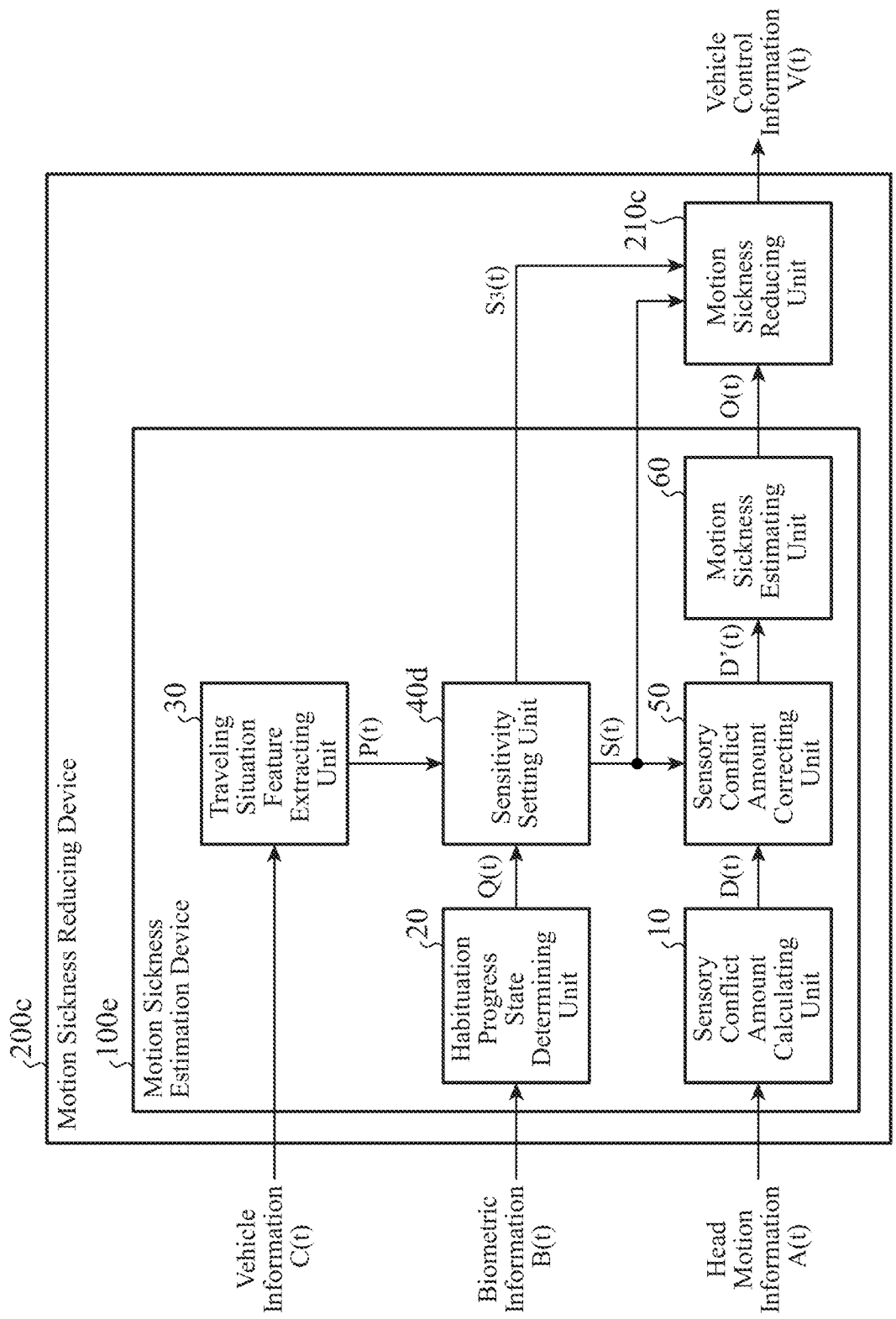
FIG. 11 is a block diagram illustrating a schematic configuration of a motion sickness reducing device according to a sixth embodiment of the present disclosure.

FIG. 11 is a block diagram illustrating a schematic configuration of a motion sickness reducing device according to a sixth embodiment of the present disclosure. The motion sickness reducing device 200c illustrated in FIG. 11 is different from the motion sickness reducing device 200 illustrated in FIG. 11 in that it includes a sensitivity setting unit 40d instead of the sensitivity setting unit 40, includes a motion sickness estimation device 100e instead of the motion sickness estimation device 100, and includes a motion sickness reducing unit 210c instead of the motion sickness reducing unit 210. In FIG. 11, the same or a corresponding component as that illustrated in FIG. 9 is denoted by the same symbol as that in FIG. 9. Meanwhile, description of the same or a corresponding component as or to that illustrated in FIG. 9 will be omitted.

The sensitivity setting unit 40d receives a determination result of the habituation progress state Q(t) and a traveling situation pattern P(t), calculates the sensitivity S(t) of a sensory conflict amount with respect to the current traveling situation, outputs the sensitivity S(t) to the sensory conflict amount correcting unit 50 and the motion sickness reducing unit 210c, and outputs sensitivities $S_{all}(t)$ of the sensory conflict amount with respect to all traveling situation patterns to the motion sickness reducing unit 210c.

The motion sickness estimation device 100e receives head motion information A(t), biometric information B(t), and vehicle information C(t) as input and outputs, to the motion sickness reducing unit 210c, the sensitivity S(t) of the sensory conflict amount with respect to the current traveling situation, the sensitivities $S_{all}(t)$ of the sensory conflict amount with respect to all the traveling situation patterns, and the motion sickness level O(t).

The motion sickness reducing unit 210c receives the sensitivity S(t) of the sensory conflict amount with respect to the current traveling situation, the sensitivities $S_{all}(t)$ of the sensory conflict amount with respect to all the traveling situation patterns, and the motion sickness level O(t) as input and outputs vehicle control information V(t).

The motion sickness reducing unit 210c is the same as in the fourth embodiment in that it outputs vehicle control information V(t) so that the motion sickness level decreases when the motion sickness level becomes high. In addition, the motion sickness reducing unit 210c generates the vehicle control information V(t) so that the traveling situation pattern P(t) is not classified into a traveling situation pattern of a high sensitivity S(t) on the basis of the sensitivity S(t) of the sensory conflict amount with respect to the current traveling situation, the sensitivities $S_{all}(t)$ of the sensory conflict amount with respect to all the traveling situation patterns, and the motion sickness level O(t). Furthermore, the motion sickness reducing unit 210c generates the vehicle control information V(t) so that the traveling situation pattern P(t) is classified into a traveling situation pattern of a low sensitivity S(t) on the basis of the sensitivity S(t) of the sensory conflict amount with respect to the current traveling situation, the sensitivities $S_{all}(t)$ of the sensory conflict amount with respect to all the traveling situation patterns, and the motion sickness level O(t).

According to the motion sickness reducing device of the sixth embodiment, it is possible to suppress motion sickness of an occupant by outputting vehicle control information so that the motion sickness level is lowered when the motion sickness level becomes high and that the traveling situation pattern P(t) is classified into a traveling situation pattern of a low sensitivity S(t) on the basis of the sensitivity S(t).

Seventh Embodiment

Figure 12:
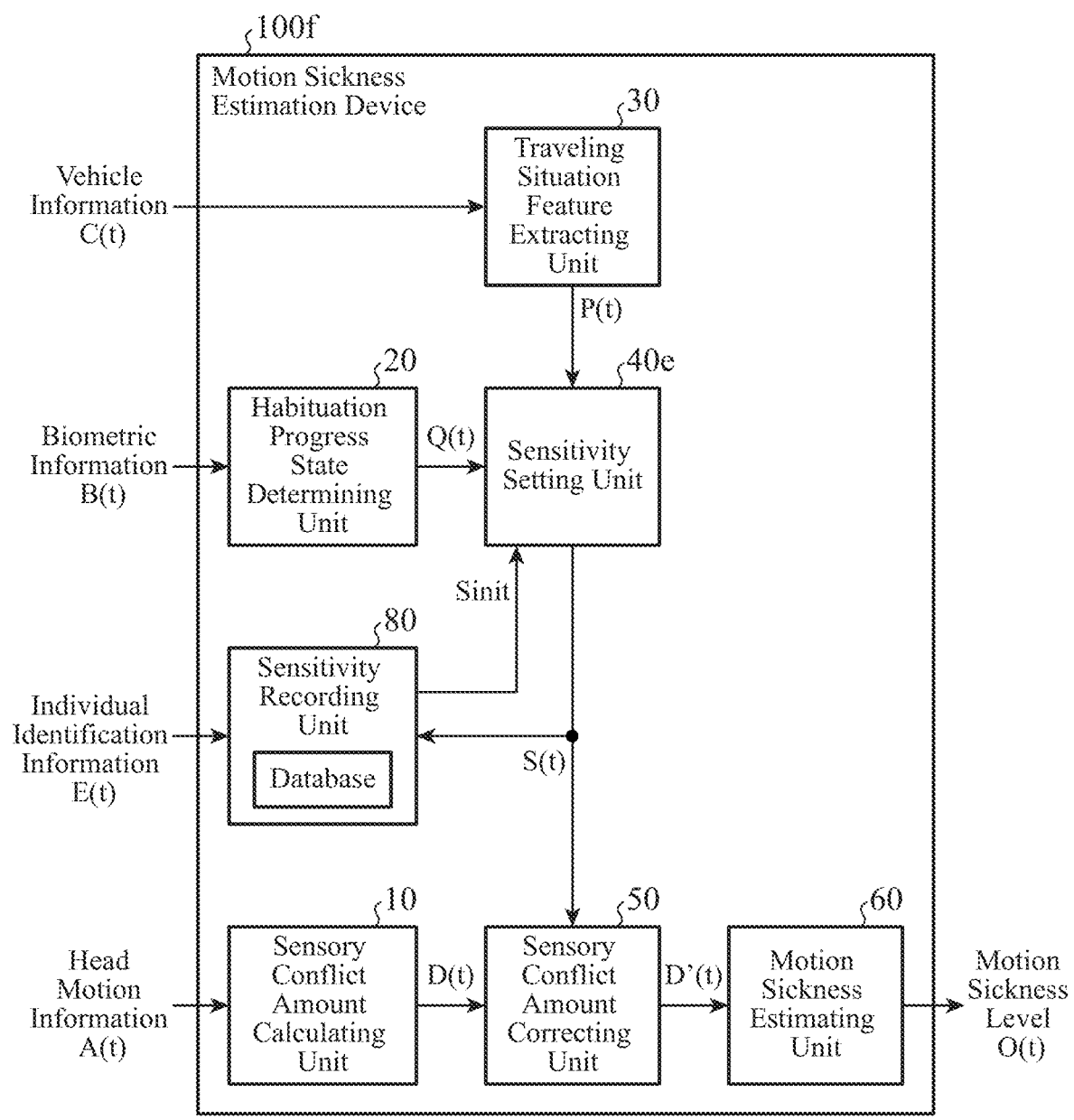
FIG. 12 is a block diagram illustrating a schematic configuration of a motion sickness reducing device according to a seventh embodiment of the present disclosure.

FIG. 12 is a block diagram illustrating a schematic configuration of a motion sickness estimation device 100f according to a seventh embodiment of the present disclosure. The motion sickness estimation device 100f illustrated in FIG. 12 includes the motion sickness estimation device 100f instead of the motion sickness estimation device 100 illustrated in FIG. 1. The motion sickness estimation device 100f is different from the motion sickness estimation device 100 in that individual identification information E(t) is received as input. The motion sickness estimation device 100f is also different from the motion sickness estimation device 100 in that a sensitivity setting unit 40e is included instead of the sensitivity setting unit 40. The motion sickness estimation device 100f is further different from the motion sickness estimation device 100 in that the sensitivity recording unit 80 is included. In FIG. 12, the same or a corresponding component as that illustrated in FIG. 1 is denoted by the same symbol as that in FIG. 1. Meanwhile, description of the same or a corresponding component as or to that illustrated in FIG. 1 will be omitted.

The present embodiment is different from the first embodiment in that the sensitivity recording unit 80 receives individual identification information E(t) and sensitivity S(t) and records the sensitivity S(t) corresponding to the individual identification information E(t) in a database. The present embodiment is different from the first embodiment also in that the sensitivity recording unit 80 outputs an initial sensitivity value $S_{init}$ corresponding to the individual identification information E(t) to the sensitivity setting unit 40e. Note that the initial sensitivity value $S_{init}$ in the present embodiment is an initial value for each type of traveling situation patterns. The present embodiment is different from the first embodiment also in that the sensitivity setting unit 40e sets the initial value of sensitivity for each type of traveling situation patterns by using the initial sensitivity value $S_{init}$. Here, the individual identification information E(t) is information for identifying an occupant and is an identification code represented by an integer such as 0, 1, 2, or 3. The individual identification information E(t) will have a different value when the occupant changes. The individual identification information E(t) is an identification code obtained by distinguishing whether the occupant is registered or not registered from a face image obtained from, for example, an image by a camera. For example, the number of occupants to be registered is about five to ten for a general vehicle that is not used for business purposes but is mainly used in ordinary households. In a case of a new occupant who is not registered, this occupant is given with individual identification information E(t) that is an identification code as a "guest", for example.

The sensitivity recording unit 80 receives the individual identification information E(t) of the occupant and the sensitivity S(t) of the occupant as input. The sensitivity recording unit 80 records, in the database, the occupant's sensitivity S(t) as the initial sensitivity value $S_{init}$ for each individual identification information E(t) at the time when the individual identification information E(t) changes, that is, when the occupant changes. The sensitivity recording unit 80 also reads the initial sensitivity value $S_{init}$ corresponding to the individual identification information E(t) from the database and outputs the initial sensitivity value $S_{init}$ to the sensitivity setting unit 40e.

The sensitivity setting unit 40e receives the initial sensitivity value $S_{init}$ corresponding to the individual identification information E(t) from the sensitivity recording unit 80 and sets the initial sensitivity value $S_{init}$ to the sensitivity S(t) as the initial value. The sensitivity setting unit 40e further receives the determination result of the habituation progress state Q(t) and the traveling situation pattern P(t), calculates, as the sensitivity S(t), the sensitivity Sp(t) that corresponds to the current traveling situation pattern p on the basis of the initial sensitivity value $S_{init}$, and outputs the sensitivity S(t) to the sensory conflict amount correcting unit 50.

Next, the operation of the sensitivity recording unit 80 will be described. The sensitivity recording unit 80 receives the individual identification information E(t) of the occupant and the sensitivity S(t) of the occupant as input, uses the sensitivity S(t) that has been input as the initial sensitivity value $S_{init}$ of the occupant, and records, in the database, the individual identification information E(t) and the initial sensitivity value $S_{init}$ of the occupant in association with each other. By recording the initial sensitivity value $S_{init}$ in a traveling situation pattern p that corresponds to the individual identification information E(t), for example, at the time when the sensitivity S(t) is updated, the most recent sensitivity S(t) for each occupant can be recorded.

Moreover, with the operation of the sensitivity recording unit 80 as described above, the sensitivity setting unit 40e can use the value of sensitivity, as of the time when the occupant has boarded in the past, as the initial value of the sensitivity calculation. Note that, in a case where there is no initial sensitivity value $S_{init}$ that corresponds to the individual identification information E(t), that is, there is no record in the database in advance, for example, the initial sensitivity value $S_{init}$ in the traveling situation pattern p is set to 1.0 and thereby output to the sensitivity setting unit 40e.

Note that in a case of a plurality of occupants, each of the head motion information A(t), the biometric information B(t), and the individual identification information E(t) input to the motion sickness estimation device 100f include the same number of pieces of information as the number of the occupants. In this case, the sensitivity recording unit 80 outputs the initial sensitivity value $S_{init}$ associated with the individual identification information E(t) of each occupant. The sensitivity setting unit 40e calculates each sensitivity S(t) using a determination result of the habituation progress state Q(t) generated from biometric information B(t) of each the occupants and the initial sensitivity value $S_{init}$ associated with the individual identification information E(t) of the occupant. For the sensory conflict amount D(t) and the corrected sensory conflict amount D'(t) as well, motion sickness levels O(t) of the plurality of occupants are calculated by generating information for each of the occupants. The operation of each component in the above description is the same except that the process is performed a plurality of times for the number of occupants.

According to the motion sickness estimation device according to the seventh embodiment, it is possible to take over calculation data as of the time when a same occupant has previously boarded the vehicle by using a value of the sensitivity when the occupant has boarded the vehicle in the past as the initial value of sensitivity calculation of the occupant, thereby enabling more efficient determination of the motion sickness state.

Figure 13:
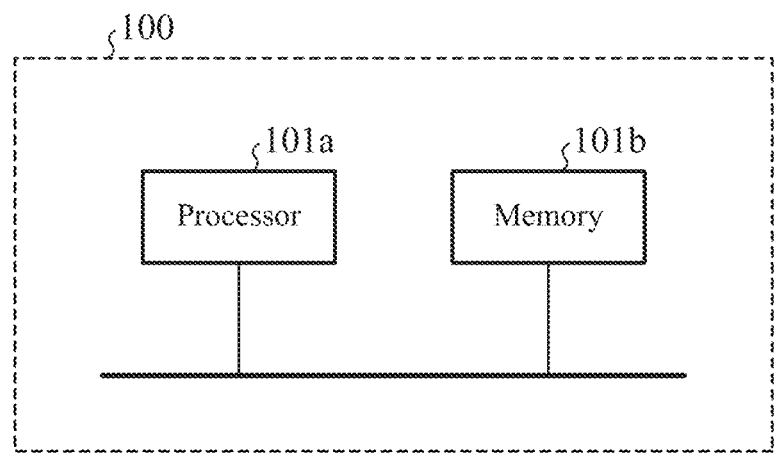
FIG. 13 is a diagram illustrating an example of a hardware configuration of a motion sickness estimation device according to the embodiment of the present disclosure.
Figure 14:
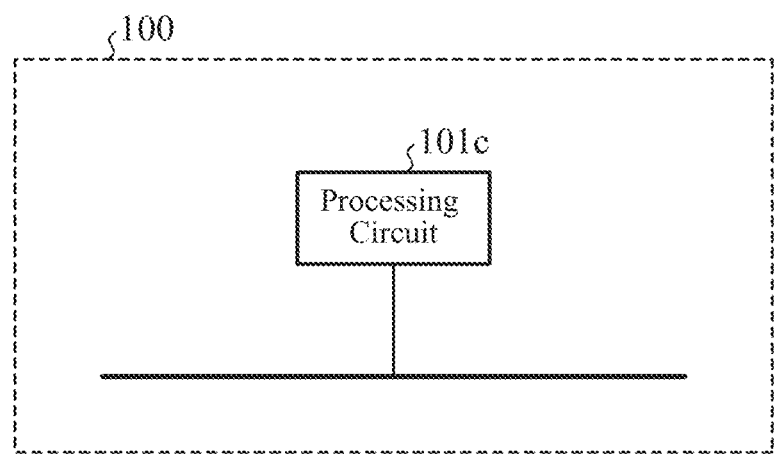
FIG. 14 is a diagram illustrating another example of the hardware configuration of the motion sickness estimation device 100 according to the embodiment of the present disclosure.

FIG. 13 is a diagram illustrating an example of the hardware configuration of the motion sickness estimation device 100. FIG. 14 is a diagram illustrating another example of the hardware configuration of the motion sickness estimation device 100.

The motion sickness estimation device 100 includes, for example, at least one processor 101*a* and a memory 101*b*. The processor 101*a* is, for example, a central processing unit (CPU) for executing a program stored in the memory 101*b*. In this case, the function of the motion sickness estimation device 100 is implemented by software, firmware, or a combination of software and firmware. The software and the firmware can be stored as a program in the memory 101*b*. With this configuration, the program for implementing the function of the motion sickness estimation device 100 (for example, the motion sickness estimation method described in the present embodiment) is executed by a computer.

The memory 101*b* is a computer-readable recording medium and may be, for example, a volatile memory such as random access memory (RAM) and a read only memory (ROM), a non-volatile memory, or a combination of a volatile memory and a non-volatile memory.

The motion sickness estimation device 100 may include a processing circuit 101*c* as dedicated hardware such as a single circuit or a composite circuit. In this case, the function of the motion sickness estimation device 100 is implemented by the processing circuit 101*c*.

Although the embodiments of the present disclosure have been described above, the present disclosure is not limited to these embodiments.

REFERENCE SIGNS LIST

100, 100*b*, 100*c*, 100*d*, 100*e*, 100*f*: motion sickness estimation device, 10: sensory conflict amount calculating unit, 20, 20*b*: habituation progress state determining unit, 30: traveling situation feature extracting unit, 40, 40*b*, 40*c*, 40*d*, 40*e*: sensitivity setting unit, 50: sensory conflict amount correcting unit, 60: motion sickness estimating unit, 70: occupant state determining unit, 80: sensitivity recording unit, 200, 200*b*, 200*c*: motion sickness reducing device, 210, 210*b*, 210*c*: motion sickness reducing unit, A(t): head motion information, B(t): biometric information, C(t): vehicle Information, Im(t): image information, O(t): motion sickness level, P(t): traveling situation pattern, Q(t): determination result of habituation progress state, R(t): occupant state information, S(t): sensitivity, U(t): autonomic nervous system state, V(t): vehicle control information

The invention claimed is:

1. A motion sickness estimation device comprising:
    processing circuitry configured to
    calculate a sensory conflict amount on a basis of a motion of an occupant's head caused by vibration of a vehicle;
    extract a feature of a traveling situation on a basis of at least one of the motion of the occupant's head or a motion of the vehicle;
    determine a habituation progress state, which is a state in which the occupant's habituation to the traveling situation has progressed, on a basis of biometric information of the occupant;
    set sensitivity to the feature of the traveling situation on a basis of the habituation progress state;
    correct the sensory conflict amount on a basis of the sensitivity; and
    estimate a motion sickness state of the occupant on a basis of the sensory conflict amount that has been corrected, wherein
    the processing circuitry is further configured to control the vehicle to reduce the motion sickness of the occupant on a basis of an estimation result of the motion sickness.

2. The motion sickness estimation device according to claim 1,
    wherein the processing circuitry determines a state of an autonomic nervous system of the occupant and determines the habituation progress state on a basis of the state of the autonomic nervous system.

3. The motion sickness estimation device according to claim 2,
    wherein the processing circuitry determines that the habituation has progressed on a basis of a fact that the state of the autonomic nervous system is in parasympathetic dominance in which a parasympathetic nervous system is dominant.

4. The motion sickness estimation device according to claim 2,
    wherein the processing circuitry is further configured to determine a state of the occupant, and
    determine the habituation progress state on a basis of the state of the occupant in addition to the state of the autonomic nervous system.

5. The motion sickness estimation device according to claim 4,
    wherein the processing circuitry determines whether or not the occupant is in an awakened state, and
    the processing circuitry determines a state in which the habituation has progressed in a case where the state of the autonomic nervous system is in the parasympathetic dominance in which the parasympathetic nervous system is dominant, and the state of the occupant is in the awakened state.

6. The motion sickness estimation device according to claim 2,
    wherein the processing circuitry classifies the traveling situation into a predetermined traveling situation pattern, and
    sets the sensitivity to each of the patterns.

7. The motion sickness estimation device according to claim 6,
wherein the processing circuitry is further configured to record, as an initial sensitivity value of the occupant, occupant identification information for identifying the occupant and the sensitivity of the occupant that are associated with each other,
wherein the processing circuitry sets by using the initial sensitivity value associated with the occupant as an initial value of sensitivity when an occupant who has been identified in a past boards the vehicle again.

8. The motion sickness estimation device according to claim 2,
wherein the processing circuitry sets a small sensitivity to the traveling situation pattern when it is determined that the habituation has progressed.

9. The motion sickness estimation device according to claim 2,
wherein the processing circuitry sets high sensitivity to the traveling situation pattern when determining that the state of the autonomic nervous system is in sympathetic dominance in which a sympathetic nervous system is dominant.

10. The motion sickness estimation device according to claim 2,
wherein the processing circuitry estimates the motion sickness state on a basis of the state of the autonomic nervous system in addition to the sensory conflict amount that has been corrected.

11. The motion sickness estimation device according to claim 10,
wherein the processing circuitry estimates the motion sickness state on a basis of the state of the occupant in addition to the sensory conflict amount and the state of the autonomic nervous system.

12. The motion sickness estimation device according to claim 1, further comprising:
a sensor that detects the motion of the occupant's head caused by the vibration of the vehicle.

13. The motion sickness estimation device according to claim 12, wherein the sensor includes an acceleration sensor or a gyro sensor that is attached to the occupant or attached to an item worn by the occupant.

14. The motion sickness estimation device according to claim 12, wherein the sensor includes a camera or a time-of-flight (TOF) sensor.

15. A motion sickness reducing device comprising:
the motion sickness estimation device according to claim 1; and
processing circuitry configured to
reduce the motion sickness of the occupant on a basis of an estimation result of the motion sickness.

16. The motion sickness reducing device according to claim 15,
wherein the processing circuitry controls the vehicle so that a traveling situation pattern, to which the sensitivity is high, and a traveling situation pattern, to which the sensitivity is low, are alternately repeated.

17. A motion sickness estimation comprising:
estimating a sensory conflict amount on a basis of a motion of an occupant's head caused by vibration of a vehicle;
extracting a feature of a traveling situation related to motion sickness from the traveling situation on a basis of at least one of the motion of the occupant's head or a motion of the vehicle;
determining a habituation progress state, which is a state in which the occupant's habituation to the traveling situation has progressed, on a basis of biometric information of the occupant;
setting sensitivity to the feature of the traveling situation on a basis of the habituation progress state;
correcting the sensory conflict amount on a basis of the sensitivity;
estimating a motion sickness state of the occupant on a basis of the sensory conflict amount that has been corrected; and
controlling the vehicle to reduce the motion sickness of the occupant on a basis of an estimation result of the motion sickness.

18. A motion sickness estimation device comprising:
processing circuitry configured to
calculate a sensory conflict amount on a basis of a motion of an occupant's head caused by vibration of a vehicle;
extract a feature of a traveling situation on a basis of at least one of the motion of the occupant's head or a motion of the vehicle;
determine a habituation progress state, which is a state in which the occupant's habituation to the traveling situation has progressed, on a basis of biometric information of the occupant;
set sensitivity to the feature of the traveling situation on a basis of the habituation progress state;
correct the sensory conflict amount on a basis of the sensitivity; and
estimate a motion sickness state of the occupant on a basis of the sensory conflict amount that has been corrected, wherein
the processing circuitry controls the vehicle so that a traveling situation pattern, to which the sensitivity is high, and a traveling situation pattern, to which the sensitivity is low, are alternately repeated.

* * * * *